(12) United States Patent
Hart et al.

(10) Patent No.: US 10,871,440 B2
(45) Date of Patent: Dec. 22, 2020

(54) MICROFLUIDIC CHIP DEVICE FOR OPTICAL FORCE MEASUREMENTS AND CELL IMAGING USING MICROFLUIDIC CHIP CONFIGURATION AND DYNAMICS

(71) Applicant: Lumacyte, LLC, Charlottesville, VA (US)

(72) Inventors: Sean Hart, Keswick, VA (US); Colin Hebert, Charlottesville, VA (US)

(73) Assignee: Lumacyte, LLC, Charlottesville, VA (US)

( * ) Notice: Subject to any disclaimer, the term of this patent is extended or adjusted under 35 U.S.C. 154(b) by 0 days.

(21) Appl. No.: 16/394,530

(22) Filed: Apr. 25, 2019

(65) Prior Publication Data
US 2019/0250093 A1    Aug. 15, 2019

Related U.S. Application Data

(63) Continuation-in-part of application No. 15/853,763, filed on Dec. 23, 2017.

(51) Int. Cl.
*G01N 15/14* (2006.01)
*B01L 3/00* (2006.01)
(Continued)

(52) U.S. Cl.
CPC .... *G01N 15/1484* (2013.01); *B01L 3/502761* (2013.01); *G01N 15/00* (2013.01);
(Continued)

(58) Field of Classification Search
CPC ............. G01N 15/1434; G01N 15/147; G01N 15/1484; G01N 21/85; G01N 21/05; G01N 2015/1445; G01N 2015/1006; G01N 2201/06113; B01L 3/5027; B01L 3/502761; B01L 3/502715; B01L 2300/0654; B01L 2400/0487; B01L 2400/0433; B01L 2400/043; B01L 2400/0418;
(Continued)

(56) References Cited

U.S. PATENT DOCUMENTS 6,321,791 B1    11/2001  Chow
6,321,971 B1 *  11/2001  Jin ................... H01L 21/67144
                                                             228/6.2
(Continued)

OTHER PUBLICATIONS

Non-Final Office Action from counterpart U.S. Appl. No. 15/853,763 dated Aug. 27, 2019.
(Continued)

*Primary Examiner* — Michael P LaPage
(74) *Attorney, Agent, or Firm* — DLA Piper LLP (US)

(57) ABSTRACT

Provided are methods and devices for assessing biological particles for use in cell immunotherapy. By utilizing a microfluidic chip device together with optical force measurement and cell imaging, the methods enable comprehensive assessment and characterization of biological particles with regard to morphology, motility, binding affinities, and susceptibility to external forces, including but not limited to, chemical, biochemical, biological, physical and temperature influences. The methods enable the selection and production of biological particles, such as engineered T-cells, for use in immunotherapy and biomanufacturing.

20 Claims, 19 Drawing Sheets

(51) Int. Cl.
*G01N 15/00* (2006.01)
*G01N 15/10* (2006.01)
*A61F 2/30* (2006.01)

(52) U.S. Cl.
CPC ............... *A61F 2002/30677* (2013.01); *B01L 2200/0652* (2013.01); *G01N 2015/1006* (2013.01)

(58) Field of Classification Search
CPC ....... B01L 2300/0874; B01L 2200/027; B01L 2300/0861; B01L 2200/10; B01L 2200/0652; B81B 1/00
See application file for complete search history.

(56) References Cited

U.S. PATENT DOCUMENTS

| | | | |
|---|---|---|---|
| 7,068,875 | B2 | 6/2006 | Wang et al. |
| 7,835,000 | B2 | 11/2010 | Graves et al. |
| 2005/0002025 | A1* | 1/2005 | Goto ................... B81C 99/0085 356/246 |
| 2009/0140170 | A1 | 6/2009 | Nevill et al. |
| 2010/0093078 | A1* | 4/2010 | Wang .................... C12M 21/02 435/325 |
| 2010/0152050 | A1* | 6/2010 | Gordon .............. G01N 21/6428 506/4 |
| 2014/0085898 | A1 | 3/2014 | Perrault, Jr. |
| 2014/0193892 | A1 | 7/2014 | Mohan et al. |
| 2014/0220557 | A1* | 8/2014 | Hart ................... G01N 33/4833 435/6.1 |
| 2015/0316188 | A1 | 11/2015 | Parkinson |
| 2017/0022558 | A1* | 1/2017 | Banyai ................. C12C 1/6874 |

OTHER PUBLICATIONS

International Preliminary Report on Patentability from corresponding PCT International Appln. No. PCT/US2017/068373 dated Jul. 2, 2020.
International Search Report and Written Opinion from corresponding PCT International Appln. No. PCT/US2017/068373 dated May 15, 2018.
Non-Final Office Action from counterpart U.S. Appl. No. 15/853,763 dated Aug. 26, 2020.

* cited by examiner

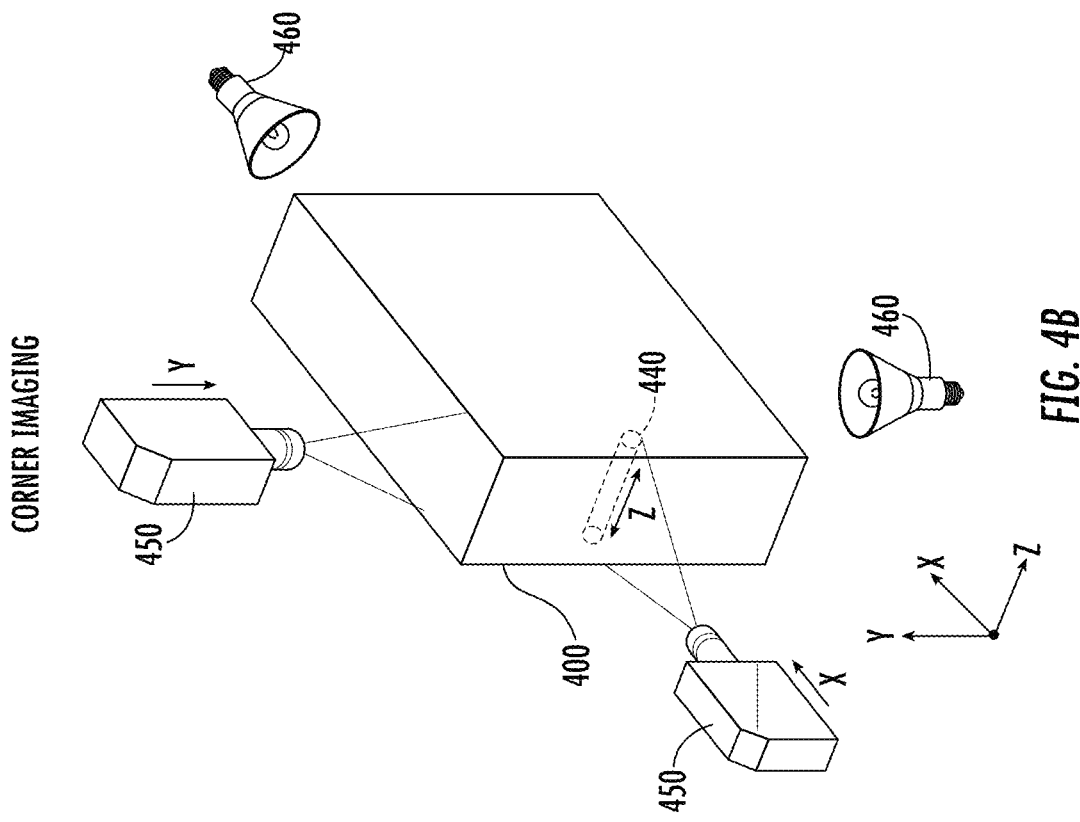
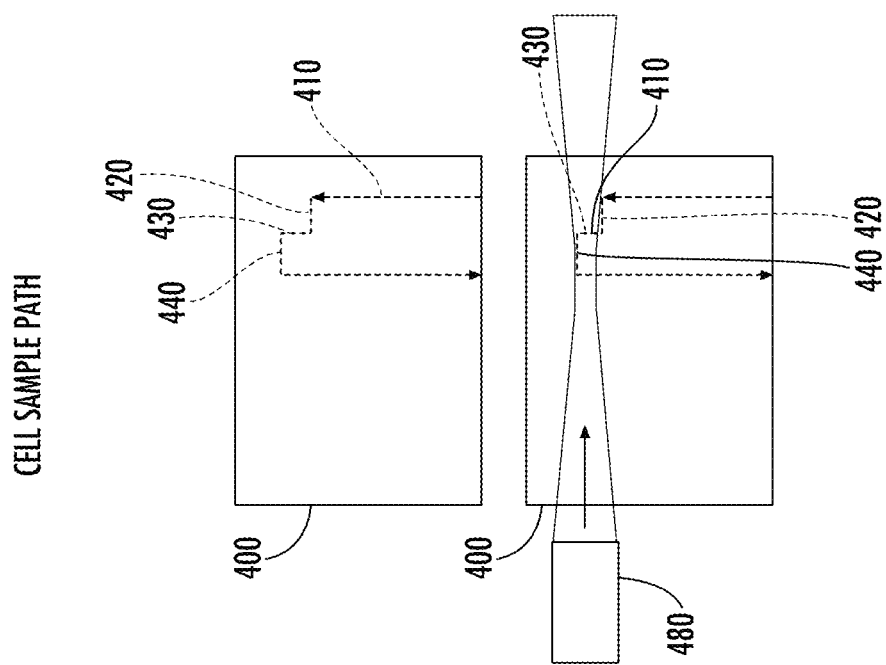
FIG. 4B
FIG. 4A

MICROFLUIDIC CHIP DEVICE FOR OPTICAL FORCE MEASUREMENTS AND CELL IMAGING USING MICROFLUIDIC CHIP CONFIGURATION AND DYNAMICS

CROSS REFERENCE TO RELATED APPLICATIONS

This application is a continuation-in-part application of U.S. patent application Ser. No. 15/853,763 filed Dec. 23, 2017 and is related to PCT/US17/68373 filed Dec. 23, 2017; both applications are incorporated by reference herein in their entirety.

BACKGROUND

Field of the Invention

This invention relates in general to a device and method for particle analysis and imaging for particles or cells in fluids, and in particular to a device and method for particle imaging for fluids using pressure, fluid dynamics, electrokinetic, and optical forces. The invention further relates to particle analysis for purposes of cell therapy. The device and methods provided herein comprise the use and application of laser force cytology microfluidic designs for analyzing and sorting cells in cell therapy (i.e. immunotherapy) applications.

The present invention is directed to a microfluidic chip wherein injection occurs in an upwards vertical direction, and fluid vials are located below the chip in order to minimize particle settling before and at the analysis portion of the chip's channels.

Changes had to be made to existing microfluidic chip designs to implement the invention herein. For example, to keep the vials vertically in-line with the chip, a different interface with the chip had to be established as compared to the prior art. Specifically, instead of the input tube interfacing with the chip via a port attached to the largest face of the chip (as is typically done in microfluidic lab-on-a-chip systems) in an orthogonal manner and then pumping fluid first across and then up the chip, the current invention has the input and fluid coming up through the bottom of the chip, in one aspect using a manifold, which avoids horizontal re-orientation of fluid/fluid dynamics.

According to the invention herein, the contents of the vial are located below the chip and pumped upwards and vertically directly into the first channel of the chip. A long channel extends from the bottom of the chip to near the top of the chip. Then the channel takes a short horizontal turn but the new channel is so short as to almost negate any influence of cell settling due to gravity and zero flow velocity at the walls. Then, contrary to the prior art, the fluid is pumped up to the analysis portion. The horizontal analysis portion is therefore the highest channel/fluidic point in the chip and thus close to the top of the chip, which results in less chip material (e.g., glass) between the microscope/camera and the sample than the prior art and therefore clearer imaging. The laser also suspends cells in this channel during analysis which prevents them from settling.

Description of the Related Art

According to the prior art, microfluidic chip vials containing cells or particles to be separated and/or analyzed are located to the side and horizontally pumped into the channels in the microfluidic chip. First the contents of the vials (e.g., particles or cells) were pumped in the upwards vertical direction, then make a u-turn to travel down, and are then pumped horizontally into the chip. (See, e.g., U.S. Pat. No. 9,594,071.)

The connection to the chip is horizontal, which, combined with the dead volume (empty space in fluidic connections that is to some extent unavoidable) in the connection, led to significant additional settling due to gravity. Such a configuration also necessitates a relatively large diameter channel required by the connection, which, in addition to the dead volume, creates an area of relatively low velocity, further increasing the problem of particle settling. The current chip according to the present invention eliminates the need for a large horizontal input channel and a rather abrupt change from a large horizontal input channel to the relatively thin upward flow in the first vertical chip channel. Such a configuration eliminates the horizontal settling and an unnecessary change in direction which causes settling. Having the cells enter the bottom edge of the chip also solves the issue of settling in the dead volume by orienting it vertically with respect to gravity so that the cells or particles cannot settle in the bottom of a horizontal channel, but rather they are constantly guided upwards by the flow. This is not intuitive and required much experimentation to realize the problem before designing the current embodied solution. Currently available microfluidic devices incorporate custom or commercially available connections on the polished surface and larger area of the glass, in contrast to the present invention, which generally forces any particles, such as cells, contained within the sample stream to take an immediate turn and travel horizontally upon entering the chip.

Also in the prior art, the cells or particles have several horizontal runs on a microfluidic chip before reaching the analysis channel, which leads to settling. At the point the vial contents enter the chip and the channels in the chip, the contents are pumped horizontally compared to the vertical in-chip channel. The channel then flows upwards and takes a long horizontal turn at which point the cells tend to settle at the bottom of the channel due to gravity, as well as experience lower velocity at the wall due to laminar flow conditions. In essence, due to parabolic velocity profile, the flow is highest in the middle of a channel and decreases to zero at or near the channel wall. After the first horizontal in-chip channel, the fluid takes a downward turn before the analysis channel where the particles are imaged or separated. Due to this configuration, there exists a relatively large distance between the microscope/camera and the analysis channel. In this typical prior art configuration, the particles are forced downward and ultimately exit the bottom of the chip.

Moreover, due to constraints in the prior art, multiple horizontal runs are required, causing cells to settle in multiple places in the channels. This, in turn, causes a decrease in image quality because of the need to image through additional material at the edge of the chip. The prior art channels in the chip had to be pumped in the upwards vertical direction, then horizontal, then in a zigzag nature for adequate cell or particle suspension, then down and out the chip. Zigzag channels are obviated by the current invention.

Prior art also exists regarding rendering 3D images of cells or particles in fluid. For example, M. Habaza, M. Kirschbaum, C. Guernth-Marschner, G. Dardikman, I. Barnea, R. Korenstein, C. Duschl, N. T. Shaked, Adv. Sci. 2017, 4, 1600205, teaches trapping a cell, rotating it at high speeds, and using interferometry to measure refractive index distribution within a cell. Interferometry has also been used to analyze cells in microfluidic channels (see e.g., Y. Sung et al., Phys. Rev. Appl. 2014 Feb. 27; 1: 014002). The current invention, however, claims taking multiple images of a cell or particle as it travels in the fluid flow and passes through the focal planes of the imaging device(s), thereby negating any need to trap the cell in order to render a 3D image. Other techniques have been taught, such as moving a cell or particle using a mechanical translation stage (e.g., N. Lue et al., Opt. Express 2008 Sep. 29; 16(20): 16240-6), none of which use bright field imaging as described herein and do not utilize fluid flow to provide cell positioning relative to the image focal plane.

The current state of the art for single cell analysis for cell therapy relies on cumbersome labeling constructs such as antibodies or genomic labels (e.g. green fluorescent protein) for the ability to detect cellular changes. What is needed however, is a methodology that is label-free and capable of detecting subtle or unknown phenotypic changes in cells. What is also needed is the ability to assess characteristics of cells intended for various purposes, including but not limited to cell therapy, wherein the cells may be quickly and accurately assessed for a multitude of phenotypic attributes, such as morphology, motility, interaction with other physiological components and reaction to environmental changes.

All prior art references cited herein are incorporated by reference in their entirety.

SUMMARY OF THE INVENTION

The present invention is directed to a microfluidic chip wherein injection occurs and sample vials are located below the chip in order to minimize particle settling. Therefore, the contents of the vial are located below the chip and pumped upwards and vertically directly into the channel of the chip. A long channel extends from the bottom of the chip to near the top of the chip. Then the channel takes a short horizontal turn but the new channel is sufficiently short as to be insignificant with respect to any influence of cell settling due to zero flow velocity at the walls of the channel. Then, contrary to the prior art, the sample is pumped up to the analysis portion. The horizontal analysis portion is therefore the highest channel/fluidic point in the chip and thus close to the top of the chip, which results in less glass between microscope/camera than the prior art and therefore clearer imaging. Distance of the analysis channel from the top of the chip may be from 100 microns to 2 mm, but as great as 100 mm such as from 100 microns to 200 microns, from 200 microns to 300 microns, from 300 microns to 400 microns, and so on. In one embodiment, after the analysis portion of the chip, the sample, e.g., fluid, cells, and/or particles, are pumped downwards to the bottom of the chip and forced outwards.

The present invention is further directed to a microfluidic chip wherein horizontal runs are minimized, especially at the point fluid enters in the chip channels. Prior art chips contain about 13 mm in horizontal channels (non-analysis portions), around 2 mm of which is of the much larger diameter injection port, exacerbating settling due to the low velocity. The chip described herein has, in a preferred embodiment, about 0.2 to 3.0 mm in horizontal channels (non-analysis), although the horizontal channels may range in length from 0.01 to 100.0 mm, such as from 0.01 mm to 0.02 mm, from 0.02 mm to 0.03 mm, from 0.03 mm to 0.04 mm, and so on. This is a result of the invented channel system and is an order of magnitude different from the prior art, which improves flow and elimination of cell/particle settling.

Another aspect of the invention is directed to a microfluidic chip wherein imaging occurs and analysis is based at or near the corner of the chip, whereby imaging from multiple viewpoints is improved because less glass and distance exists between the camera and analysis channel. This also allows a higher numerical objective lens to be used to improve detailed imaging by increasing magnification. Such a design improvement decreases the distortion of the image caused by glass (or other substance comprising the chip, such as plastic or any transparent or semi-transparent material) and distance (e.g., due to imperfections in glass). The distance between the imaging device and analysis channel may be from 100 microns to 2 mm, but as great as 100 mm, such as from 100 microns to 200 microns, from 200 microns to 300 microns, from 300 microns to 400 microns, and so on.

Further, the present invention is directed to a microfluidic sorting chip with separation downstream from an analysis channel allowing for using both pressure and/or a laser (or other optical force) simultaneously or sequentially separately to activate a sorting function. In one aspect, flow would continue from the analysis channel for the sorting function. For example, the particles would be directed into a vertical channel and then to a horizontal sorting channel. In one embodiment, an optical force and/or pressure would be applied in the direction of the flow with the sorting channel to push particles through the channel. Particles not directly acted upon by the optical force would divert to an alternate channel due to, for example, gravity, electrokinetic forces, magnetic forces, laminar flow lines, stream lines, decreased flow rate, an orthogonal optical force, or a vacuum being applied to suck the particles into the alternate channel. In another aspect related to the sorting post-analysis channel, the present invention allows for directing an optical force from a back side of the chip (the laser or optical force being oriented in the same direction of flow) and, in some aspects, splitting this primary laser. In embodiments, the optical force and/or pressure may be applied in the opposite direction of the movement of the substance through the channel, e.g., against the flow, or may be applied in the same direction as the movement of the substance in the channel, e.g., with the flow. Cell or particle sorting could occur on a single device or a separate chip. For example, in FIG. 1B, the fifth channel prior to the outlet tubing 145, contains one or more bifurcations to enable single or multiple sorting regions.

In another aspect of the current invention, a manifold is connected to a vial in a way such that tubing goes through the manifold and connects to a vial or other vessel on the other side making contact with the substance (e.g., fluid) in the vial. The manifold allows for vials to be connected to the microfluidic chip but stored under the chip, and/or the manifold allows for contents of the vials to be injected from the bottom of the chip, alleviating several problems experienced by the prior art, such as cell or particle settlement where the vial or tubing from the vial connects to or communicates with the microfluidic chip.

In another aspect, the present invention is directed to a microfluidic chip holder, this chip holder comprising a structure to guide a light source including an integrated prism cavity, which when fitted with a prism causes light to exit at an angle relative to the chip and is a preferred method for illuminating constrained geometry. In embodiments, the light source includes but is not limited to fiber optics or a collimated or focused light source. This light source is precisely directed, or oriented, or directed into the analysis channel, in particular.

In another aspect of the current invention, the device includes a second imaging device oriented orthogonally to the first camera and channel view. Reasons for the second camera vary. In one aspect, the reason for a second imaging device is to aid in visual alignment of the laser or optical force in the analysis channel. In another aspect, using the method described herein, data from the first camera can be recorded. With the second camera, data can be combined with data from the first camera, resulting in additional data that can be used to more accurately extrapolate cell position, size, shape, volume, etc. This additional information about the same cell (or particle) increases the accuracy and range of measurements and analysis. In a further aspect, the second camera, combined with the first camera, allows for a 3D reconstruction of a cell or particle, or group of cells or particles, imaged by the orthogonal camera and a camera in the flow or a camera located towards the side of the chip. Using the algorithm described herein or others, including reversing or slowing the flow and taking one or more images of a particular cell or particle, or group of cells or particles, the invention allows for multiple images to be analyzed and processed thereby allowing for determination of characteristics/attributes/quantitative measurements, such as the cell volume, cell shape, nucleus location, nucleus volume, organelle or inclusion body location, etc. In another aspect of the current invention a camera is oriented to image in the axis that is in the direction of flow.

In one aspect, the current invention does not require a serpentine or zigzag channel, as preferred according to the prior art, to keep particles properly suspended. Because of the vertical nature of fluid and particles or cells being injected in the chip, the zigzag channel is obviated by the vertically integrated pumped particles that flow directly up through the channel to the first horizontal channel (referred to herein as the second channel).

In an embodiment, provided herein are novel methods for assessing one or more aspects of biological components, such as cells. The methods described comprise the use of laser force cytology (LFC). The basic premise of the background technology, laser force cytology (LFC), is that it utilizes the combination of microfluidics and light-induced pressure to take measurements including optical force or pressure, size, velocity, and other parameters on a per cell basis (While LFC represents one embodiment of the invention, other optical force-based technologies may be used according to the present invention). The methods provided herein eliminate the use of cumbersome labelled techniques such as antibodies or genomic labels (e.g. green fluorescent protein) for the ability to detect cellular changes. Provided instead are novel methods that are label-free and capable of detecting subtle phenotypic changes in cells. The methods enable the assessment of characteristics of cells intended for various purposes, including but not limited to cell therapy, wherein the cells may be quickly and accurately assessed for a multitude of phenotypic attributes, such as morphology, motility, interaction with other physiological components and reaction to environmental changes. In certain embodiments, the methods utilize LFC for the analysis of cell therapy products before and during biomanufacturing.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

FIGS. 4A and 4B are diagrams showing examples of the cell path and imaging configuration related to the chip.

DETAILED DESCRIPTION

Figure 1A:
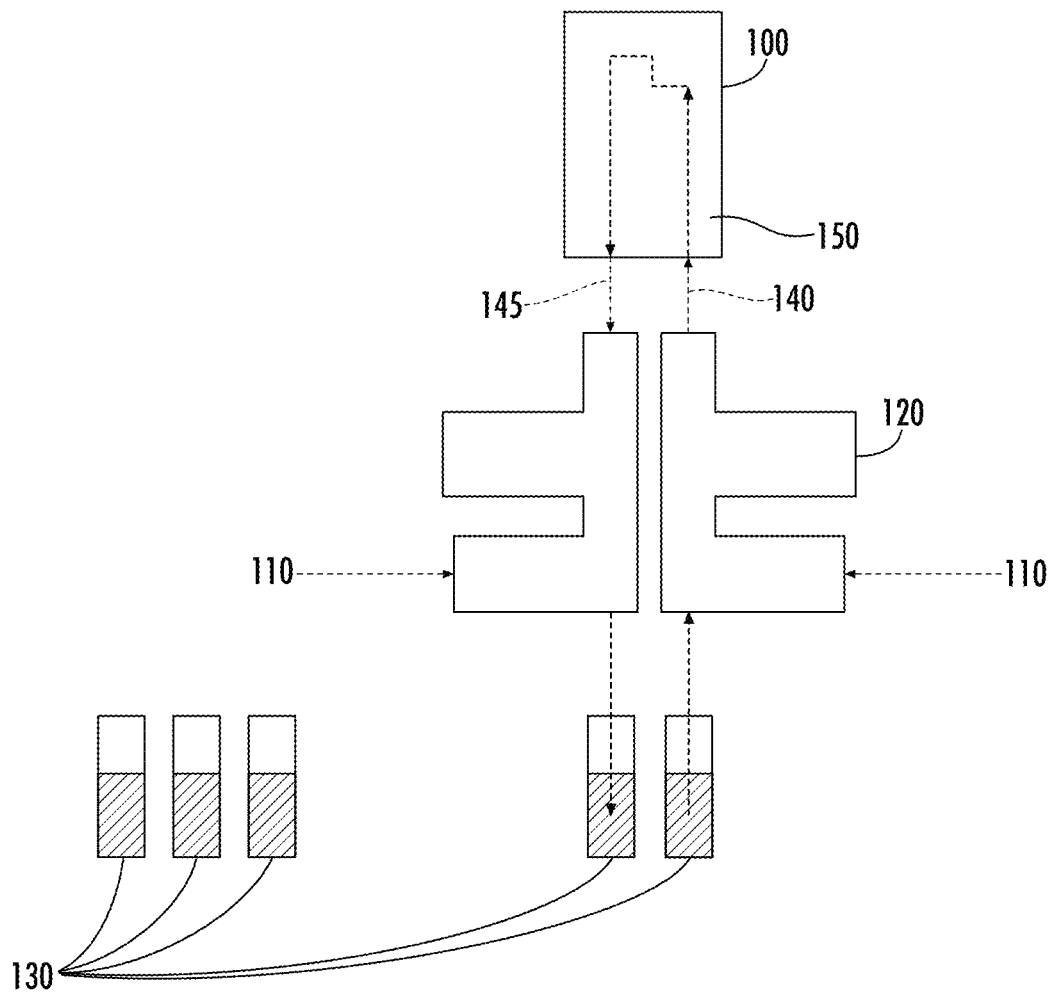
FIG. 1A is a diagram depicting a global view of the device configuration, including the chip, manifold, and vials.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary or explanatory in nature and, thus, variations that do not depart from the essence of the invention are intended to be within the scope of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
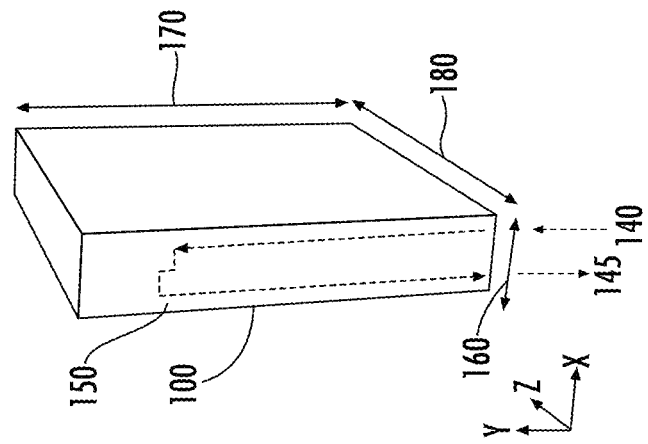
FIG. 1B is a diagram which shows certain depictions of the chip channel orientations and locations.

Turning now to the figures, FIG. 1A shows a global view of the device taught herein. The sample vials 130 are located below the microfluidic chip 100 (which may also be referred to generically herein as a substrate) and are not limited in terms of number of vials or sizes. The vials are configured to hold any type of sample that can be moved through the device, such as one or more substance, including but not limited to one or more of fluids, liquids, gas, plasma, serum, blood, cells, platelets, particles, etc. or combinations thereof. In the context of this specification, the term fluid or sample may be used generically to refer to such one or more substances. The vials are connected either directly or indirectly, such as indirectly using air tubing 110 in operable communication with the underside of the chip. They may also be connected by way of a manifold 120 as further shown in FIG. 1A. FIG. 1B shows a preferred embodiment of the microfluidic chip 100 whereby the substance, fluid, particles, and/or cells is/are injected at one exterior surface, such as an edge, of the microfluidic chip (e.g., the XZ plane in FIG. 1B). Injection is shown in FIG. 1B along one of the faces shared by the smallest distance, such as the XZ face or the XY face. In this particular embodiment, the length of side X 160 is less than the length of side Y 170 and the length of side Z 180. Such a configuration allows a sample to have minimal deviation upon entering channels on the chip (e.g., no right turn is necessary as is generally the case in current state of the art).

In FIG. 1A, a manifold 120 is shown connecting the vial or vials 130 to the microfluidic chip 100 so that the substance, fluid, particles, and/or cells may be injected or pumped into the microfluidic chip in the vertical and upwards direction. The manifold allows injection of substances from the bottom of the chip, while also positioning the electronics, flow sensors, and tubing (both liquid and air) in such a way as to minimize cell settling, which optimizes throughput. Air tubing provides pressure or vacuum, which, when sealed, provides for a closed system within the confines of the manifold apparatus. In one embodiment there is a distance between the vial(s) and the manifold indicating that there is no seal and the pressure of the internal volume is atmospheric. This allows for pumping substances from or to a container open to the atmosphere (vacuum is required to pump from an open container). The manifold positions the electronics, flow sensors, and tubing (both liquid and air) in such a way as to minimize cell settling which optimizes throughput.

By injecting the contents from the bottom of the chip, the invention minimizes horizontal movement in inlet tubing 140 and outlet tubing 145, which causes such problems as settlement of the particles or cells in the channel(s) 150. The outlet tubing is offset from the inlet tubing, in this example, in the Z and X dimensions (FIG. 1B). In embodiments, the outlet tubing is offset, not offset, straight, in-line, or angled in relation to the inlet tubing. Such a configuration obviates the need for serpentine or zigzag vertical channels because the current configuration resolves problems with settlement that occur in the prior art, such as in the case in which fluid combined with cells and/or particles is injected or pumped into the chip from the side in a horizontal direction that then must change direction and fluid dynamics to be pushed upwards. The manifold and injection from the bottom of the chip also allow for additional elements, components, machinery, or hardware to be placed below the chip. (See FIG. 1A.)

The manifold 120 works by adjusting the air pressure above the contents in the vial and providing correct geometry for flow sensors and electronics. Tubing, such as fluid or air tubing, passes through the manifold and connects to a vial on the other side. Pressurized air passes through one side of manifold and creates a closed pressurized system within the manifold. By adjusting pressure in the enclosed region, the system allows for changes to parameters such as flow speed and fluid dynamics. The pressurized region is in both the vial(s) 130 and the manifold 120. In another aspect, no air connection is needed for the vial, because it is open to the ambient atmosphere. This enables sampling of a larger variety of containers and sources. In such an embodiment, a vacuum is applied to the other one or more vials such that a pressure differential is created to drive fluid flow from the open container.

In one embodiment, pressure-based sample injection is used. The vials are filled with a sample in a fluid and sealed either with a lid or tubing connected to the chip. Prior to attachment to the lid, the vial can be either open to the air or sealed with a septum or other gas-tight device. In one aspect, the lid may contain two connections, one for a fluid such as a gas and one for a liquid. Optionally, the method embodiment further includes providing a sample inlet line tip communicating with a sample inlet line, which communicates with the first channel.

In another embodiment, a vacuum based sample injection is used. The vials are filled with a sample in a fluid and sealed either with a lid or tubing connected to the chip. Prior to attachment to the lid, the vial can be either open to the air or sealed with a septum. In one aspect, the lid may contain two connections, one for a fluid such as a gas and one for a liquid. Optionally, fluid can be aspirated from a vial open to the atmosphere by applying vacuum pressure to one or more of the other vials. Optionally, the method embodiment further includes providing a sample inlet line tip communicating with a sample inlet line, which communicates with the first channel.

In FIGS. 2A-B and 3A-B, a chip holder 200, 300 is shown. The chip holder comprises a structure to guide a light source 210, such as a fiber optic light source, light emitting diode, or laser, and an integrated prism cavity 220, 320 that can be fitted with a prism. The light source is guided or aligned by an integrated structure or channel 240 within the chip holder to the desired location. The built-in space for the fiber optic light source allows for illumination, such as a cone of illumination 250, even in constrained geometric environments, such as on a microfluidic chip 230, 330 or a channel in a microfluidic chip. This light source is precisely directed, or oriented, or focused on the analysis channel 260 in particular, in a preferred aspect. In a preferred embodiment, the chip holder includes a built-in space for a prism 220, 320 and fiber optic light source 210 allowing for illumination with constrained geometry. The chip further includes holes or openings in the bottom of the holder 350 to precisely align fluidic tubing as described herein. In one embodiment, adjustable screws are integrated into threaded holes 360 on one or more faces for proper alignment.

FIG. 4A is a preferred embodiment of the microfluidic chip 400 described herein. As shown, fluid travels first upwards in a vertical direction through a first channel 410 then communicates with a second horizontal channel 420. Another vertical channel 430 takes the fluid even closer to the top of the chip at which point a fourth channel 440 is horizontal and, as show in the FIG. 4, comprises the analysis channel. The channels are in operable communication with one another to allow for a sample to be moved through the system from one channel to another. In embodiments the sample can flow from the first channel to the second channel to the third channel to the fourth channel, or in the reverse, or combinations thereof. A pump and/or vacuum apparatus can be provided to provide positive and/or negative pressure at either or both the opening and the exit of the channels to enable movement of the substances through the channels. The analysis channel is close to one or more exterior surface of the substrate, such as the faces, edges, or sides of the chip. For example, the analysis channel, according to this configuration, is close to the top and side of the chip, thereby improving imaging and analysis through the substance of the microfluidic chip. In preferred embodiments, the analysis channel is from around 1 mm to around 2 mm from the top and side of the chip. However, the distance of the analysis channel from the top of the chip may be from 0.1 mm to 100 mm, such as from 0.1 mm to 0.2 mm, from 0.2 mm to 0.3 mm, from 0.3 mm to 0.4 mm, and so on. Expressed another way, the analysis channel can be disposed within the top 50%, 33%, 25%, 10%, or 5% of the substrate. The length of the horizontal analysis channel according the present invention may be from around 250 microns to around 10 mm. However, the length of the analysis channel may be from 100 microns to 100 mm, such as from 0.1 mm to 0.2 mm, from 0.2 mm to 0.3 mm, from 0.3 mm to 0.4 mm, and so on. Expressed another way, the length of the analysis channel can be about 75% or less of the height, width or length of the substrate/chip, such as 50% or less, 33% or less, 25% of less, 10%, or 5% or less of the height, width or length of the substrate/chip.

In FIG. 4B, two imaging devices 450, such as machine vision cameras, are shown. In one embodiment, a camera may be located above the chip and be oriented orthogonally to the analysis channel. In another embodiment, a camera may be located to the side of the chip and be oriented orthogonal to the direction of the flow or diagonal to the direction of the flow (such as above the channel, below the channel, or at angles to the side of the channel). In embodiments, the camera can be positioned such that the imaging is performed at any angle relative to the flow of the one or more substance, such as orthogonal or 90 degrees relative to the flow of the one or more substance, or such as from 0 to 90 degrees, or from 10 to 80 degrees, or from 30 to 60 degrees and so on. In another embodiment, two or more cameras may be used to image cells or particles in the analysis channel. For example, a camera may be above the chip and be oriented orthogonally to the analysis channel. A second camera may be located to the side of the chip and be oriented orthogonally to the direction of the flow or diagonal to the direction of the flow (such as above the channel, below the channel, or angles to the side of the channel). As pictured in FIG. 4B, one or more light sources 460 may be used to illuminate the analysis channel 440, and such light sources may be located under the chip and shining up, to the side of the chip and shining in the flow direction or opposite the flow direction, above the chip and shining down, or diagonally to the analysis channel.

Figure 8:
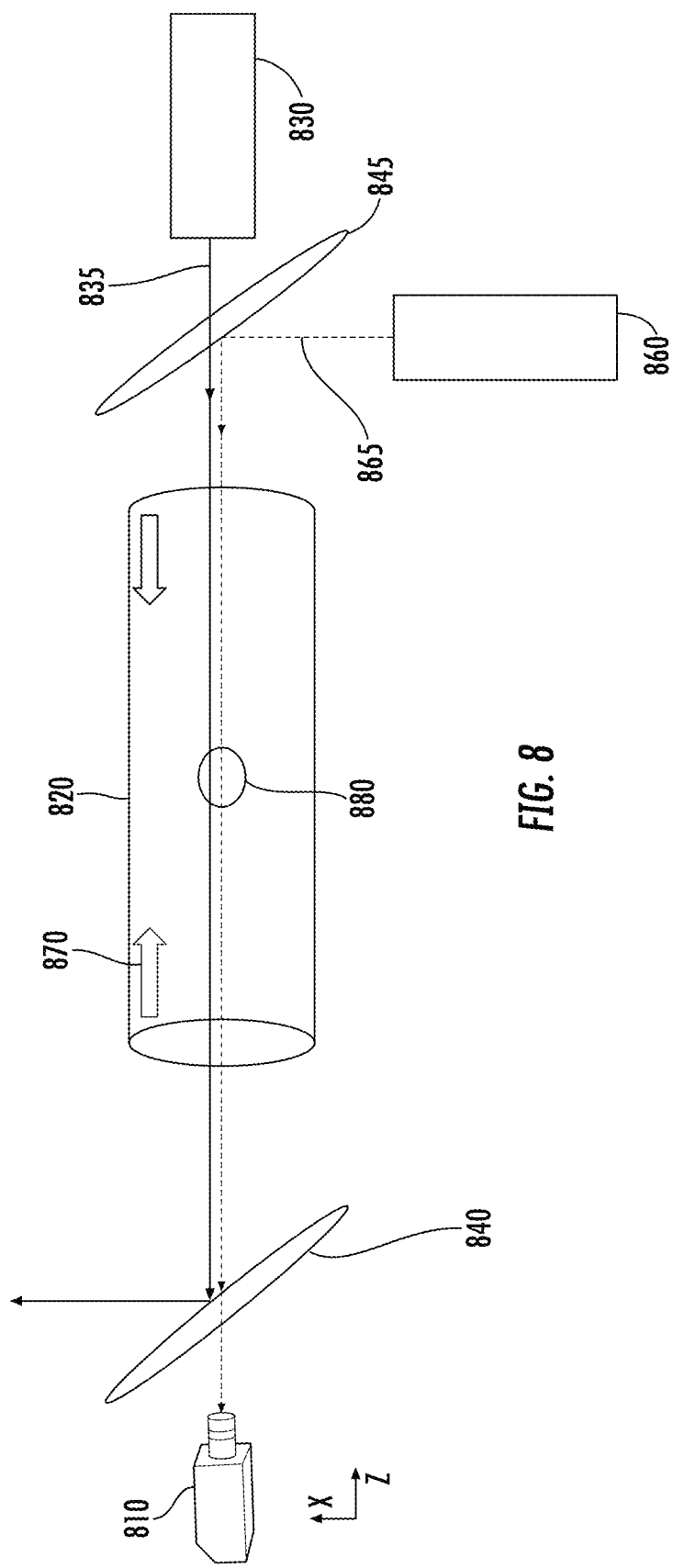
FIG. 8 is a diagram showing how a camera and illumination source can be placed in line with the laser and direction of flow, such that the particles move away from the camera.
Figure 9:
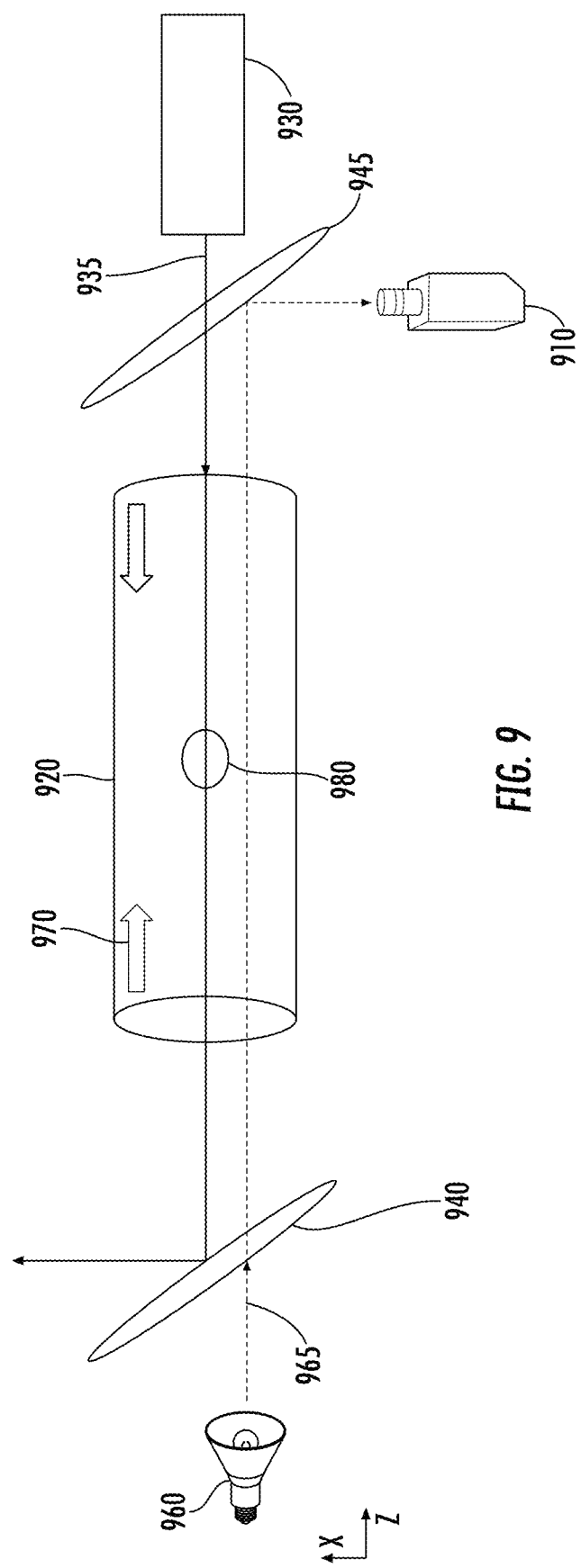
FIG. 9 is a diagram showing how a camera and illumination source can be placed in line with the laser and direction of flow, such that the particles move toward the camera.

Alternatively, a dichroic mirror 840 or other appropriate optical element can be used to selectively divert a specific wavelength range of light while allowing others to pass, such as shown in FIG. 8. This would allow for cameras 810 to be placed in line with the analysis channel. As pictured in FIGS. 8 and 9, several embodiments of this occur, including placing the optical force laser 830 and camera 810 at the same or opposite ends of the analysis region. An illumination source 860 for the camera might also be required and can be oriented in several ways, such as what is shown in FIGS. 8 and 9. The light source could be a broad spectrum source, such as one or more LEDs or a narrow source such as a laser. The camera could be used as a single camera or as part of a multi-camera system in combination with other viewpoints as described herein.

Also pictured in FIG. 4A, a light source 480, such as a laser, may be used to affect cell flow. The laser may be placed in line with the cell flow, or opposing the cell flow. The laser may also be placed and/or oriented orthogonally or diagonally to the cell flow.

An embodiment of the invention includes a device for particle analysis. (See, e.g., FIGS. 4-9.) The embodiment of the invention includes at least one camera 450 for capturing images of particles or cells in the microfluidic channels (e.g., 440). In one embodiment, a laser or other optical force 480, such as a collimated light source operable to generate at least one collimated light source beam, is included. The at least one collimated light source beam includes at least one beam cross-section. The embodiment of the invention includes a substrate with a first channel 410 extending in a vertical direction in the substrate such that a first plane traverses first channel 410 substantially along its length and whereby the fluid sample is injected into the substrate/chip from the bottom of the chip and is forced by positive or negative pressure upwards. The embodiment of the invention includes a second channel 420 orthogonal to the first channel and thus disposed horizontally in the substrate such that a second plane traverses second channel 420 substantially along its length and the second plane is disposed orthogonal to the first plane. This second channel is in the horizontal direction of the chip. The second channel communicates directly or indirectly with the first channel. The second channel communicates directly or indirectly with a short upward vertical third channel 430 that takes the channel network closer to the top of the chip. The third channel communicates directly or indirectly with a fourth horizontal channel 440 that is located near the top and/or corner of the chip. In a preferred embodiment, the fourth channel is the channel closest to the top of the chip. In an embodiment, the fourth channel is an analysis channel. In one aspect, a camera 450 is oriented orthogonally to the flow direction in the fourth channel. The embodiment of the invention includes a focused particle stream nozzle operably connected to the first channel. In another aspect of the current invention, the second channel undergoes a size change and passes through a nozzle before communicating with the third channel.

Figure 4C:
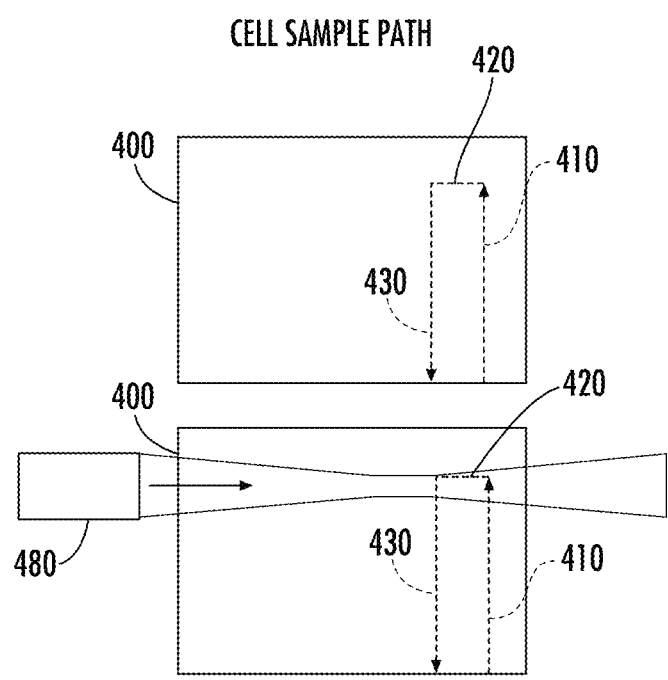
FIG. 4C is a diagram which shows an alternative cell path.

FIG. 4C shows another embodiment of the sample path of the microfluidic chip. As shown, fluid travels in the chip first upwards in a vertical direction through a first channel 410, which channel then communicates directly or indirectly with a second horizontal channel 420 at, in this example, the top of the chip and comprises the analysis channel in this embodiment. The analysis channel, according to this configuration, is close to the top of the chip, thereby improving imaging and analysis through the substance of the microfluidic chip. In preferred embodiments, the analysis channel is from around 1 mm to around 2 mm from the top and side of the chip. However, the distance of the analysis channel from the top of the chip may be from 0.1 mm to 100 mm, such as from 0.1 mm to 0.2 mm, from 0.2 mm to 0.3 mm, from 0.3 mm to 0.4 mm, and so on. Expressed another way, the analysis channel can be disposed within the top 50%, 33%, 25%, 10%, or 5% of the substrate. The length of the horizontal analysis channel according the present invention may be from around 250 microns to around 10 mm. However, the length of the analysis channel may be from 100 microns to 100 mm, such as from 0.1 mm to 0.2 mm, from 0.2 mm to 0.3 mm, from 0.3 mm to 0.4 mm, and so on. Expressed another way, the length of the analysis channel can be about 75% or less of the height, width or length of the substrate/chip, such as 50% or less, 33% or less, 25% of less, 10%, or 5% or less of the height, width or length of the substrate/chip. In embodiments, the substrate can comprise one or more analysis channel, such as 1, 2, 3, 4, 5, 6, 7, 8, 9, or 10 analysis channels.

Also pictured in FIG. 4C, a light source 480, such as a laser, may be used to affect substance flow, such as cell flow. The laser may be placed in line with the cell flow, or opposing the cell flow. The laser may also be placed and/or oriented orthogonally or diagonally relative to the cell flow.

Figure 1B:
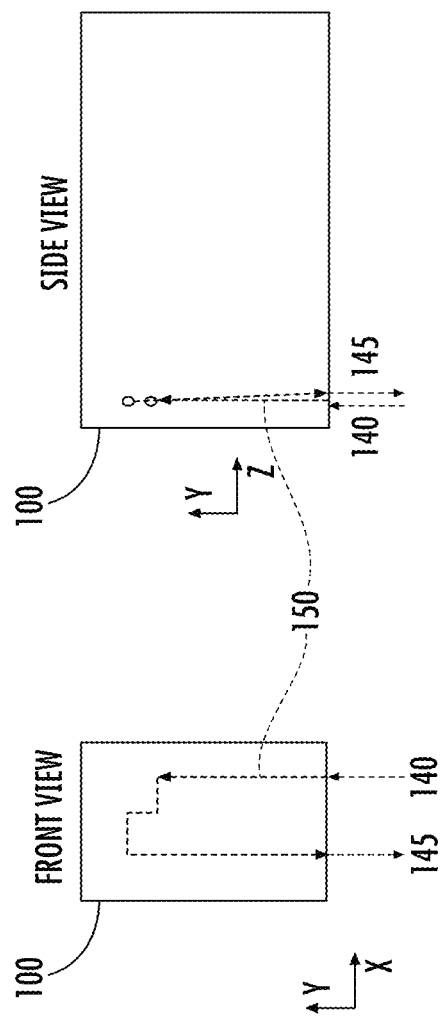
Figure 2A:
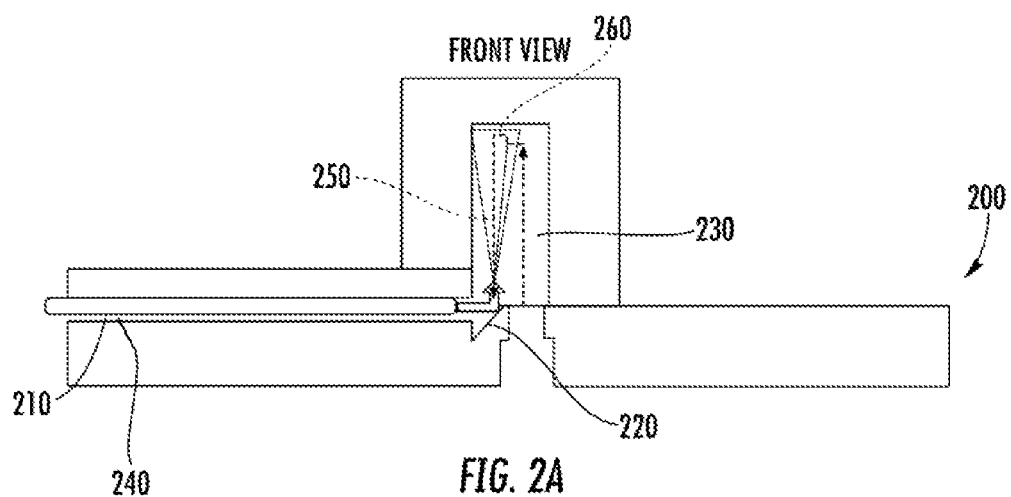
FIGS. 2A and B contain diagrams depicting the microfluidic chip holder according to the present invention.
Figure 2B:
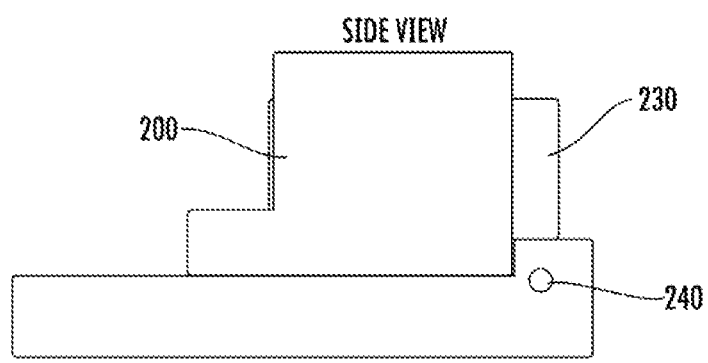
Figure 3B:
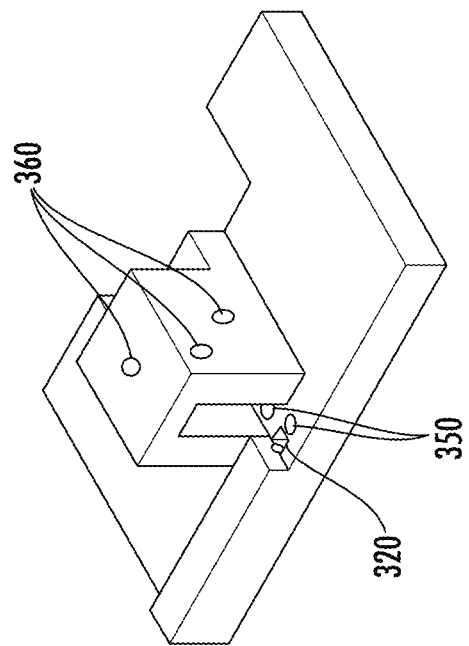
FIGS. 3A and 3B are a diagram depicting angles and aspects of the chip holder according to the present invention.
Figure 3A:
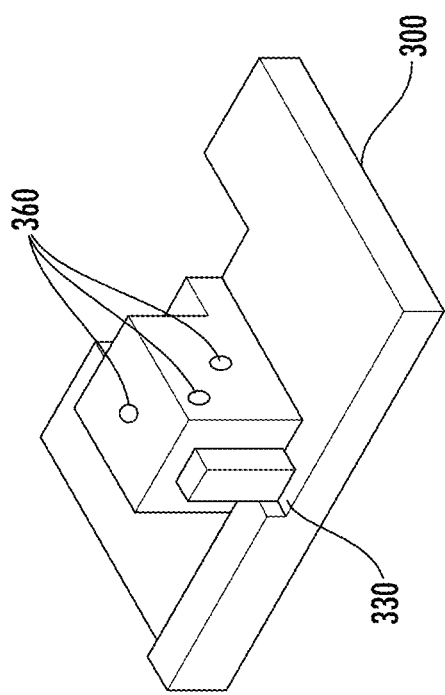

In FIGS. 1 and 4, a fluid flow containing cells or particles is directed through a first channel vertically. The one or more substance (fluid, cells, and/or particles) enter through the bottom of the chip at an opening of the first channel and enter the substrate in the vertical direction. The first vertical channel is between 100 microns and 100 mm in length, such as from 0.1 mm to 0.2 mm, from 0.2 mm to 0.3 mm, and so on. The first channel is followed by a second orthogonal/horizontal channel, which, in a preferred embodiment, is shorter than the first channel. The second channel may be 250 microns to 100 mm in length, such as from 0.25 mm to 0.5 mm, from 0.5 mm to 0.75 mm, from 0.75 mm to 1.0 mm, and so on. A third channel runs vertically and parallel to the first channel. The third channel may be 50 microns to 100 mm in length, such as from 0.05 mm to 0.1 mm, from 0.1 mm to 0.15 mm, from 0.15 mm to 0.2 mm, and so on. The channels are disposed in operable communication either directly or indirectly in such a manner as to allow one or more substance to move through multiple channels. The typical direction of the fluid flow is given by the flow arrows in FIGS. 4A and 4C, but can be reversed.

In preferred embodiments, the fourth channel comprises the analysis channel, which is a channel from 250 microns to 100 mm in length, such as from 0.25 mm to 0.5 mm, from 0.5 mm to 0.75 mm, from 0.75 mm to 1.0 mm, and so on. In this embodiment, the fourth channel is the channel closest to the top of the chip. The distance of the fourth channel from the top of the chip, measured vertically, may be from 100 microns to 2 mm, but as great as 100 mm such as from 100 microns to 200 microns, from 200 microns to 300 microns, from 300 microns to 400 microns, and so on. Expressed another way, the fourth channel can be disposed within the top 50%, 33%, 25%, 10%, or 5% of the chip. The imaging device, such as a camera, can be oriented orthogonal to the fourth channel and around 100 microns to 2 mm from the fourth channel, but as great as 100 mm from the fourth channel, such as from 100 microns to 200 microns, from 200 microns to 300 microns, from 300 microns to 400 microns, and so on.

In one embodiment, a laser or other optical source is present with a focusing lens element. FIG. 4A depicts the invention with the laser 480 operating, emitting a laser beam, directing the beam through a focusing lens element into the fourth flow channel 440. The particles are aligned within the laser beam due to the gradient force which draws particles toward the region of highest laser intensity. The laser scatter force propels particles in the direction of laser beam propagation (e.g., left to right in FIG. 4A).

In another embodiment, a second camera or image capturing device (see 450), in addition to the camera or image capturing device oriented orthogonally to the fourth channel, is oriented to the side of the analysis (or fourth) channel here and directed orthogonally or at any angle relative to the fourth channel; for example, as pictured in FIG. 4B. Taking one image of each cell at orthogonal views allows for multiple cell properties, for example size and shape, to be calculated in two dimensions, increasing the amount of information that can be captured for each cell. This would also enable the calculation of volumetric properties of the cells, including total volume, shape and give insight into cells that are not symmetric about the axis parallel to the direction of flow (the Z-axis as drawn in FIG. 5). Using two or more cameras, a basic 3D model of the cell 550 can be constructed by combining the orthogonal images using, for example, existing 3D reconstruction algorithms, such as diffraction-theory method or illumination rotation-method. A 3D model and analysis of a 3D model will allow for a more accurate analysis of the cell, such as cell size, shape, orientation, and other quantitative and qualitative measurements regarding the particle(s) or cell(s) in the fourth channel of the microfluidic chip.

Figure 5:
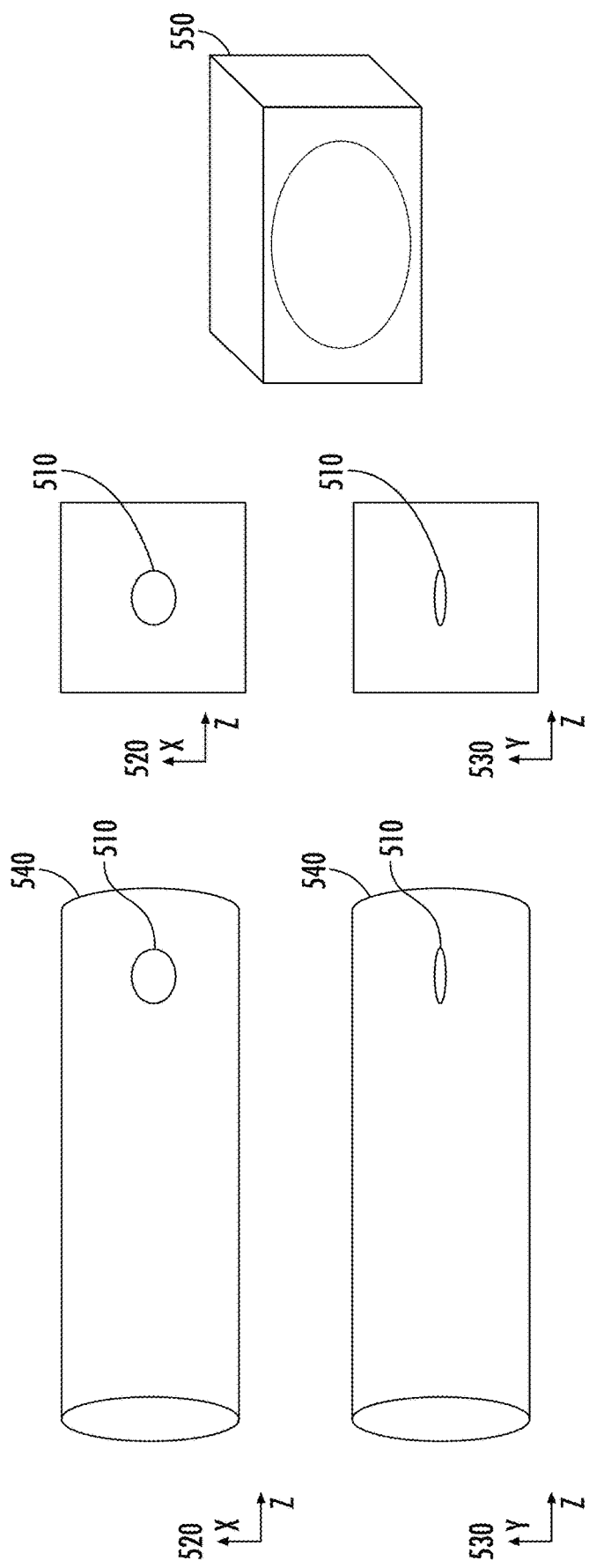
FIG. 5 is a diagram showing on chip multi-plane imaging and how it may be used to render a 3D images and information.

In FIG. 5, a portion of the analysis channel 540 is shown from two different planes, such as planes that might be imaged from an imaging device (see, e.g., FIG. 4). In the first plane 520, one part of the cell or particle 510 is imaged in a certain orientation. In the second plane 530, another part of the same cell or particle is imaged from a different perspective from another camera. This allows for the calculation of multiple cell properties, creating a matrix of data per cell per camera and a 3D rendition of the cell or particle 550.

Figure 6A:
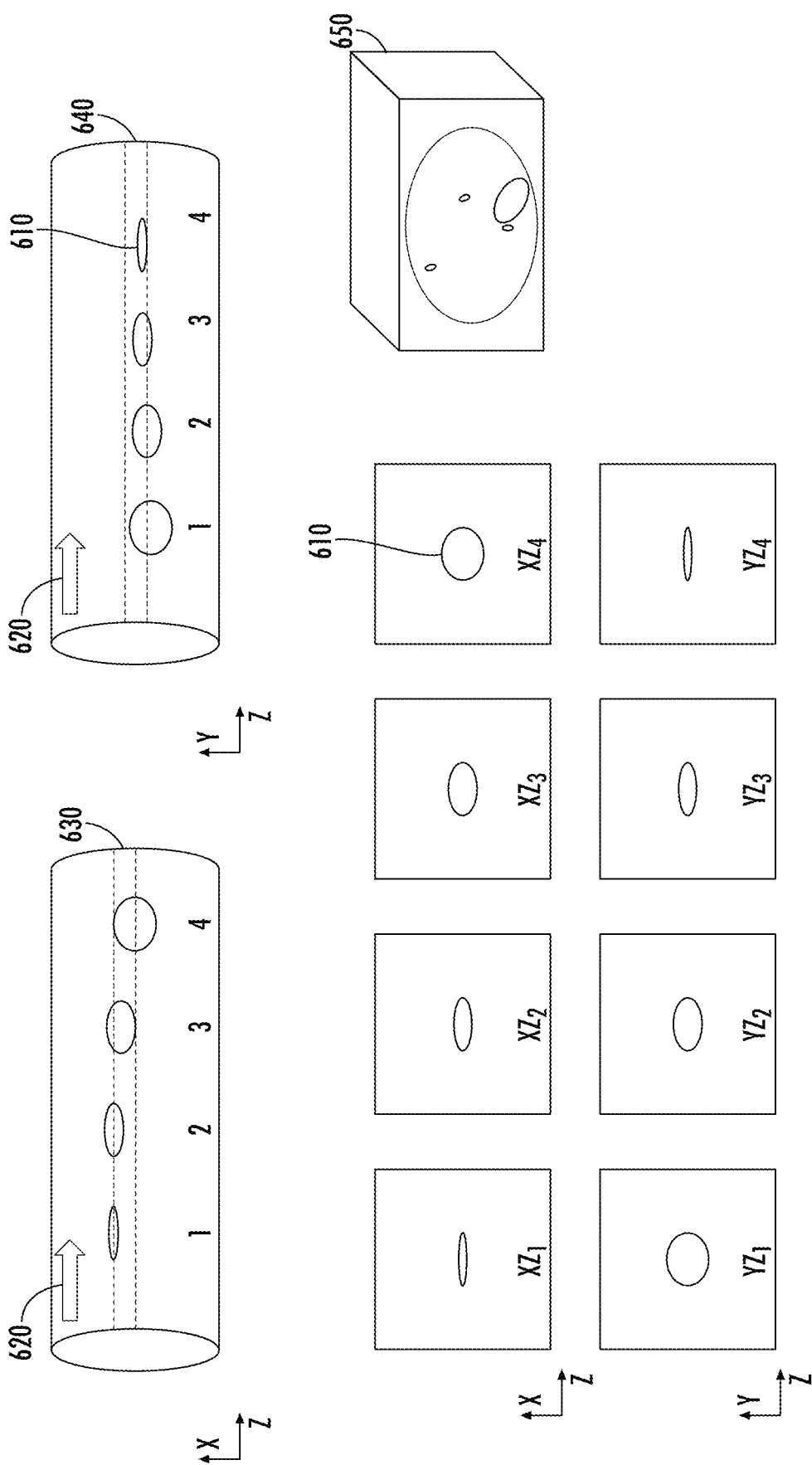
FIGS. 6A and 6B are diagrams showing on chip multi-plane imaging in fluid flow and how it may be used to render a 3D image.

As different portions of the cell pass through the focal planes (e.g., 630 (the XZ focal plane) and 640 (the YZ focal plane)) of the imaging device(s), different slices of the cell can be imaged as the cell is moved by, for example, the fluid flow 620. This is shown in FIG. 6A. In FIG. 6A, parts of the cell or particle are imaged at multiple points in time and/or space in different orientations and from different perspectives. In this example, as the cell moves and rotates through the focal plane, it appears as a different size in the successive images (such as the four example images per plane from two different cameras as shown in FIG. 6A). Using 3D reconstruction algorithms, this allows for a more complex 3D rendering 650 of the particle or cell. From such a rendering, certain attributes of the cell or particle may be extrapolated, such as cell size, volume, location and size of the nucleus as well as other organelles, and measurement or outlining of cellular topography. Additionally, cell rotation can be measured as a function of optical force based torque due to changes in biophysical or biochemical properties, including but not limited to, refractive index, birefringence, or cell shape or morphology.

Figure 6B:
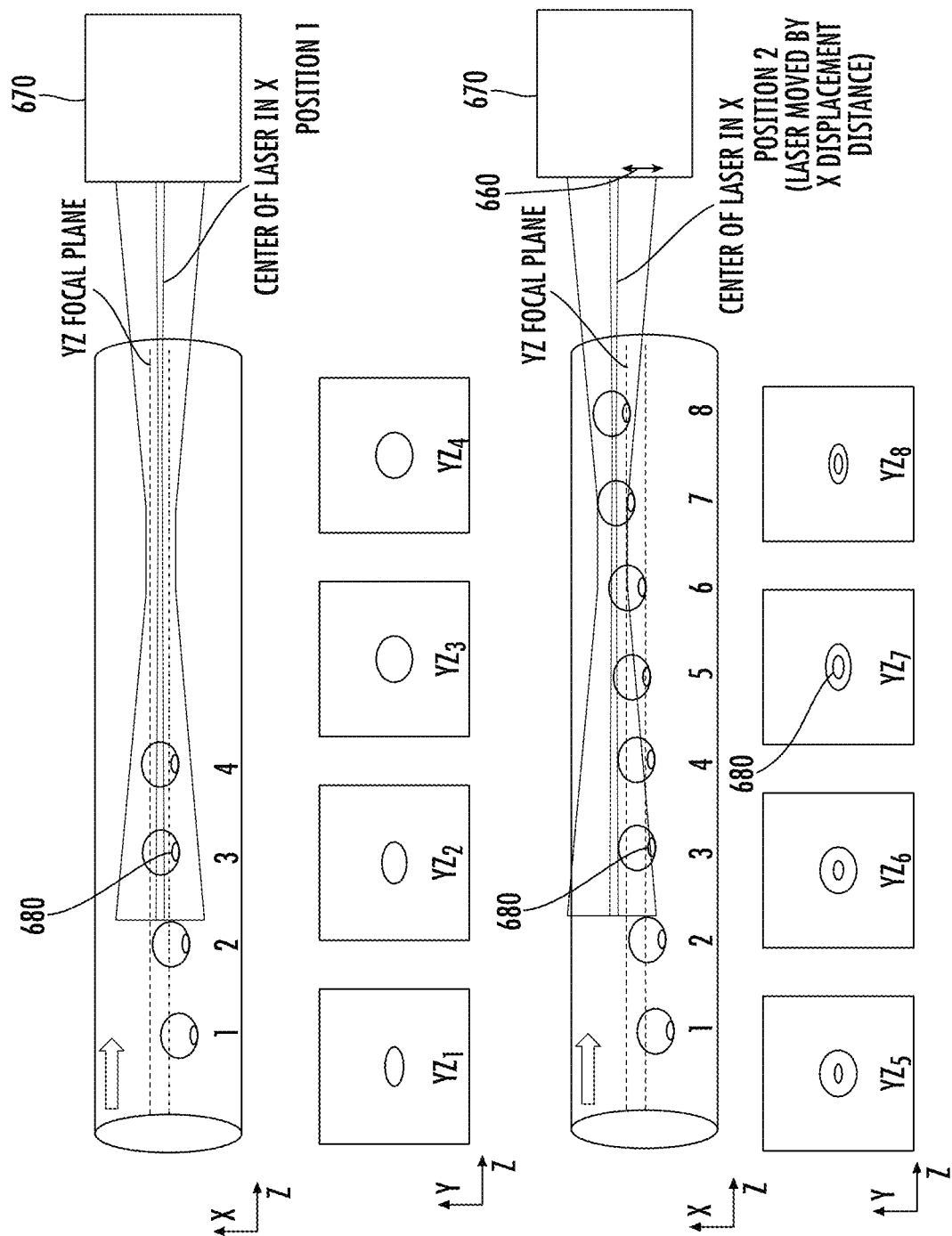

FIG. 6B depicts on chip multi-plane imaging with multiple images of the same cell being taken over time, as the cell moves through the focal plan, for example. In such cases, a view of the cell is referred to in the art as a "slice" or "image slice." An image slice is effectively the thickness of the optical plane being imaged. The thickness of the image plane, or slice, is dictated, among other things, by the optical magnification of the imaging system. At higher magnifications the working distance of the objective lens decreases resulting in the need to have the lens closer to the cell or particle to be imaged. In one embodiment, a laser or other optical force 670 may be used to affect the flow of the cell in the analysis channel. In a preferred embodiment, cells or particles may be purposefully induced into or out of the focal plane of the channel for imaging by either moving the laser and/or camera, or adjusting flow(s), or position using hydrodynamic focusing. For example, the laser source could be moved by a distance 660 using, for example, a piezo electric actuator or linear electric optomechanical stage. This could be performed on a per cell or per population basis. The hydrodynamic focusing of cells could be changed to affect the initial position and trajectory of the cells. For example, particles may be aligned or oriented in the focal plane within a laser beam due to the gradient force which draws particles toward the region of highest laser intensity. The laser scatter force propels particles in the direction of laser beam propagation. See FIG. 6B. Moving the laser, in this case in the X axis, allows for imaging of features in different parts of the cell, illustrated by the disc 680. This could represent, for example, the nucleus, organelles, inclusion bodies, or other features of the cell or particle. The laser pulls the cell to its center as a result of the gradient force. It is further contemplated that two or more cameras may increase detail and accuracy.

Figure 7:
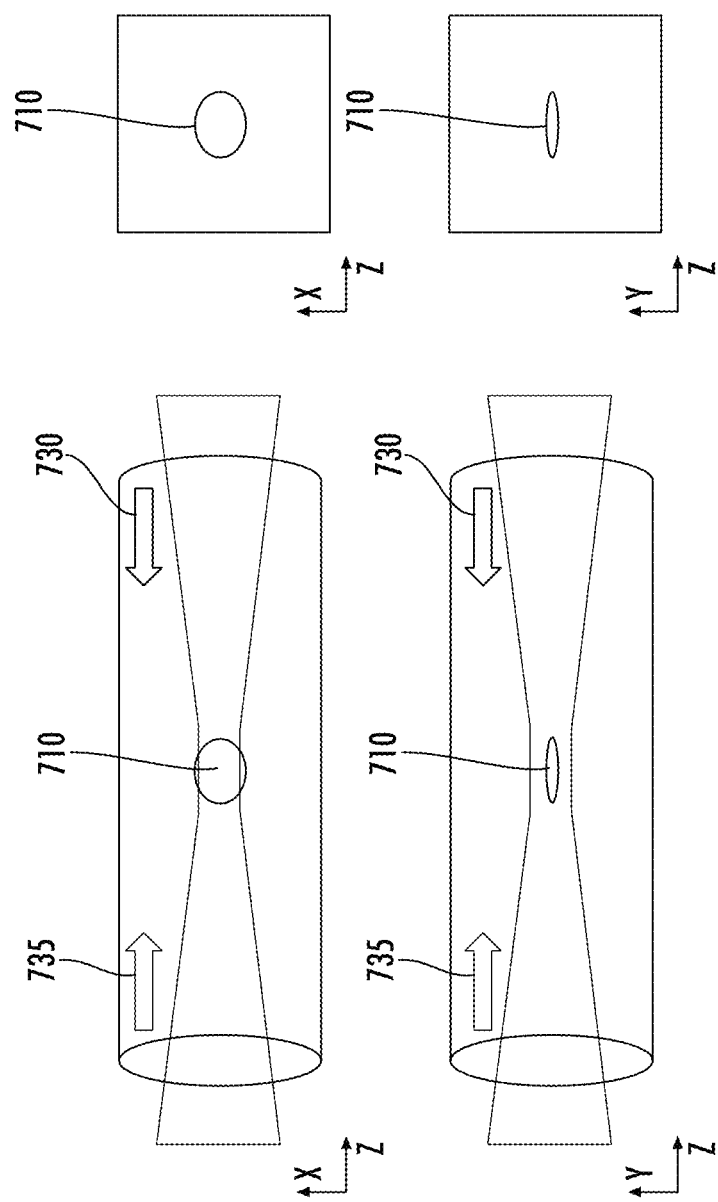
FIG. 7 is a diagram showing how a cell may be trapped and/or balanced within the analysis portion of the chip and imaged from multiple angles.

An embodiment of the invention shown in FIG. 7 is a static mode where the particle or cell 710 is stopped at a specified differential retention location by balancing the optical 730 and fluidic forces 735. The optical force may be applied by, for example, a laser or collimated light source. Images can be taken in multiple planes such as shown and described for FIGS. 5 and 6A-B. A flow sensor is used to measure the flow rate at which each particle stops in the flow for a given laser power. Because the optical and fluidic forces are balanced the fluidic drag force (i.e., from flow rate and channel dimension) is equal to the optical force. The properties of each cell can be measured sequentially in this manner. Although not a high throughput measurement system, this embodiment of the invention allows close observation and imaging of the trapped cell and also dynamic changes in optical force resulting from biochemical or biological changes in a cell. Reagent streams containing chemicals, biochemicals, cells, or other standard biological agents can be introduced into the flow channels to interact with the trapped cell(s). These dynamic processes can be quantitatively monitored by measuring changes in optical force during experiments on a single cell or cells.

In one embodiment, a camera or other imaging device is oriented and/or focused in flow or opposite the flow of the analysis channel, such that it is in line and parallel to the flow. (See, e.g., FIGS. 8 and 9.) FIG. 8 shows a camera 810 in line with the analysis channel 820 and laser or collimated light source 830. A dichroic mirror or similar device 840 reflects the laser light 835 away from the camera to prevent damage but passes light 865 produced by the illumination source 860 to allow for imaging. The camera is oriented parallel to the fluid flow 870 such that the cells or particles 880 are, in one embodiment, moving away from the camera. The illumination source is oriented orthogonal to the channel and laser. A second dichroic 845 that passes laser light and reflects illuminating light is used to direct both the illuminating light and laser light through the channel. An alternative embodiment of this configuration switches the locations of the laser and illumination source such that the laser is orthogonal to the channel and the illumination source is parallel to the channel. The second dichroic would still direct both the laser light and visible light through the channel.

An alternative embodiment is shown in FIG. 9. In this case, the camera or imaging device 910 is oriented such that the cells or particles 980 are traveling toward the camera in the fluid flow 970. Thus, the camera and laser 930 are on the same side of the channel, while the illumination source 960 is on the opposite end of the channel. Two dichroics 940 and 945 are used to direct laser light 935 and illumination light 965 into the channel, direct the illumination light to the camera, and divert the laser light away from the illumination source. An alternative embodiment of this configuration switches the locations of the laser and camera such that the laser is orthogonal to the channel and the illumination source is parallel to the channel. The second dichroic 945 would then direct the laser light through the channel and illuminating light to the camera.

Optionally, the embodiment of the invention further includes at least one optical element between a source of optical force and said fourth channel, and operable to produce a standard $TEM_{00}$ mode beam, a standard $TEM_{01}$ mode beam, a standard $TEM_{10}$ mode beam, a standard Hermite-Gaussian beam mode, a standard Laguerre-Gaussian beam mode, Bessel beam, or a standard multimodal beam. Optionally, the at least one optical element includes a standard cylindrical lens, a standard axicon, a standard concave mirror, a standard toroidal mirror, a standard spatial light modulator, a standard acousto-optic modulator, a standard piezoelectric mirror array, a diffractive optical element, a standard quarter-wave plate, and/or a standard half-wave plate. Optionally, the source of optical force may include a standard circularly polarized beam, a standard linearly polarized beam, or a standard elliptically polarized beam.

Optionally, a device is embodied comprising a microfluidic channel, a source of laser light focused by an optic into the microfluidic channel, and a source of electrical field operationally connected to the microfluidic channel via electrodes; flowing particles in a liquid through the microfluidic channel; and manipulating the laser light and the electrical field to act jointly on the particles in the microfluidic channel, thereby separating the particles based on size, shape, refractive index, electrical charge, electrical charge distribution, charge mobility, permittivity, and/or deformability. In yet another embodiment, a device comprises a microfluidic channel configured to supply a dielectrophoretic (DEP) field to an interior of the channel via an (1) electrode system or (2) insulator DEP system, and a source of laser light focused by an optic into the microfluidic channel; flowing a plurality of particles in a liquid into the microfluidic channel; and operating the laser light and field jointly on particles in the microfluidic channel to trap the particles or modify their velocity, wherein said DEP field is linear or non-linear. Another possible embodiment of a device includes a microfluidic channel comprising an inlet and a plurality of exits, and a source of laser light focused by an optic to cross the microfluidic channel at a critical angle matched to velocity of flow in the microfluidic channel so as to produce an optical force on the particles while maximizing residence time in the laser light of selected particles, thus separating the particles into the plurality of exits, wherein the laser light is operable to apply forces to particles flowing through the microfluidic channel, thereby separating the particles into the plurality of exits.

Optionally, the embodiment of the invention further includes at least one particle interrogation unit communicating with one or more of the channels, such as the analysis channel(s) and in particular the fourth channel. The particle interrogation unit includes a standard illuminator, standard optics, and a standard sensor. Optionally, the at least one particle interrogation unit includes a standard bright field imager, a standard light scatter detector, a standard single wavelength fluorescent detector, a standard spectroscopic fluorescent detector, a standard CCD camera, a standard CMOS camera, a standard photodiode, a standard photomultiplier tube, a standard photodiode array, a standard chemiluminescent detector, a standard bioluminescent detector, and/or a standard Raman spectroscopy detector.

The at least one particle interrogation unit communicating with the fourth channel comprises a laser-force-based apparatus or device that facilitates cell disease identification, selection, and sorting. In one aspect, the unit utilizes inherent differences in optical pressure, which arise from variations in particle size, shape, refractive index, or morphology, as a means of separating and characterizing particles. In one aspect, a near-infrared laser beam exerts a physical force on the cells, which is then measured. Optical force via radiation pressure, when balanced against the fluidic drag on the particles, results in changes in particle velocity that can be used to identify differing particles or changes with populations of particles based on intrinsic differences. The fluidic and optical force balance can also be used to change the relative position of particles to one another based upon their intrinsic properties thus resulting in physical separations. Another embodiment of the interrogation unit includes a device for particle analysis and/or separation, such as at least one collimated light source operable to generate at least one collimated light source beam. The at least one collimated light source beam includes at least one beam cross-section.

An embodiment of the instant invention involves the combination of several of the above-mentioned design elements discussed above in a unitary device. Embodiments also include methods of using such devices. An example of such a unitary device is illustrated in FIG. 1. The illustrated embodiment of the invention is a 5-layer structure with all 5 layers bonded to each other to yield a solid microfluidic chip, although the chip may be one structure as opposed to bonded layers. The chip could be constructed using a number of standard materials including, but not limited to, fused silica, crown glass, borosilicate glass, soda lime glass, sapphire glass, cyclic olefin polymer (COP), poly(dimethyl) siloxane (PDMS), OSTE, polystyrene, poly(methyl)methacrylate, polycarbonate, other plastics or polymers. This chip allows for sample input, hydrodynamic focusing, optical interrogation, imaging, analysis, sample exit and clear optical access for the laser light to enter and exit the regions. The chip in embodiments can also be 3D printed, molded, or otherwise shaped.

Optionally, the at least one particle type includes a plurality of particle types. Each particle type of the plurality of particle types includes respective intrinsic properties and respective induced properties. Optionally, the intrinsic properties include size, shape, refractive index, morphology, intrinsic fluorescence, and/or aspect ratio. Optionally, the induced properties include deformation, angular orientation, rotation, rotation rate, antibody label fluorescence, aptamer label fluorescence, DNA label fluorescence, stain label fluorescence, a differential retention metric, and/or a gradient force metric. This method embodiment further includes identifying and separating the plurality of particles according to the respective particle types based on at least one of the intrinsic properties and the induced properties. Optionally, this method embodiment further includes interrogating or manipulating the sample flow. Optionally, interrogating the sample flow includes determining at least one of the intrinsic properties so and the induced properties of the particle types, and measuring particle velocity of the plurality of particles. Measurement of at least one of the intrinsic properties can be used for a range of applications, including but not limiting to: determining the viral infectivity of a cell sample (the number of functionally infectious virus particles present in a particular cell population, similar to a plaque assay or end point dilution assay) for the purposes of viral quantification, process development and monitoring, sample release assays, adventitious agent testing, clinical diagnostics, biomarker discovery, determining the productivity of a cell in terms of antibody or protein for process development and monitoring, determining the efficacy, quality, or activation state of cells produced as a cell-based therapy, including CAR T and other oncology applications and stem cells, determining the effect of a chemical, bacteria, virus, antimicrobial or antiviral on a specific cell population, and determining the disease state or potential of a research or clinical cell sample. Optionally, a source of optical force includes at least one beam axis, and the sample flow includes a sample flow axis. The step of determining at least one of the intrinsic properties and the induced properties of the particle types, and the step of measuring particle velocity of the plurality of particles together comprise offsetting the beam axis from the sample flow axis. Optionally, the step of determining at least one of the intrinsic properties and the induced properties of the particle types, and the step of measuring particle velocity of the plurality of particles together comprise calculating a slope and a trajectory of a particle of the plurality of particles deviating from a sample flow axis toward at least one beam axis.

Cell-Based Immunotherapy

The immune system for most animals including mammals plays a role in recognizing and destroying infectious agents, as well as diseased and abnormal cells. The immune system is typically characterized based on two subsystems that are deployed to implement defense strategies (1) humoral system: antibodies which target antigens, such as proteins, on cell surfaces or fragments thereof, and (2) cell-mediated immunity: cells such as killer T-cells and helper T-cells that target peptides including those presented on antigens. T-cells generally function by targeting peptides that are presented on Human Leukocyte Antigen complex, or HLA. The HLA peptide complex presents peptides that are derived from intracellular target proteins. TCRs target and bind to a specific HLA peptide complex, resulting in the targeting and destruction of the relevant cell, including in many cases, cancer cells. The binding of naturally occurring T-cell receptors to cancer targets however, tends to be very poor because cancer proteins appear very similar to naturally occurring proteins and are very good at evading the immune system. Nevertheless, the utilization of cell-mediated immunity to protect against aberrant events, is gaining rapid momentum especially in the field of oncology.

Cell-based immunotherapy is a promising technological development for the treatment of human disease because it provides an opportunity to develop individualized therapeutic intervention. Although recent technical advancements have provided new gene-editing tools and the like, there is a need for precise and effective techniques for isolating, activating and expanding specific human cell types so that they may be customized for therapeutic application. The novel methods provided herein enable the characterization of cells, such as T-cells, to optimize therapeutic use and significantly improve patient outcomes. The novel methods of the invention enable a comprehensive assessment of cellular components as described above. In particular, the methods enable the development of engineered T-cells that activate or suppress immunity, by enabling the characterization of components, including but not limited, T-cell receptors, regulatory T-cells, allogeneic T-cells, bionic T-cells etc. In addition, the methods enable the characterization of T-cells with respect to binding affinities and binding profiles, specifically with regard to T-cell receptors on targets such as cancer cells. As a result, the methods herein allow for the optimization of cell-based immunotherapy by enabling the selection, enrichment and differentiation of cells, assessment of cell interaction with other agents and technologies, production of consistent cGMP cell products at commercial scale in a cost-effective manner.

Specifically, the methods herein enable the assessment and characterization of cells for efficacy assays (determined, for example, by co-culture experiments), potency assays (cell lines expressing CAR-T cells), CAR-T cell affinity studies, and CAR-T cell binding studies. The methods further enable the detection of T-cell biomarkers, as well as label-free detection of T-cell activation. In addition, the methods enable initial stock characterization, assessment of cell samples (including but not limited to whole blood, buffy coat, PBMCs, t-cells isolated, other cell fractions) as well as activation of cells using multiple parameters.

As used herein, CAR-T refers to T-cells that have been genetically engineered to produce an artificial T-cell receptor. CAR-T immunotherapy involves the modification of T cells to recognize cancer cells in order to specifically target and destroy them. In some cases, T cells are harvested from individuals with tumors, genetically altered, then infused back into the individual with the expectation that the resulting CAR-T cells will attack the tumors in the individual. CAR-T cells can be either derived from T cells in a individual's own blood (autologous) or derived from the T cells of another healthy donor (allogenic). Once isolated from an individual, T cells are genetically engineered to express a specific CAR (chimeric antigen receptor), which programs them to target an antigen that is present on the surface of tumors. For safety, CAR-T cells are engineered to be specific to an antigen expressed on a tumor that is not expressed on healthy cells.

Figure 10:
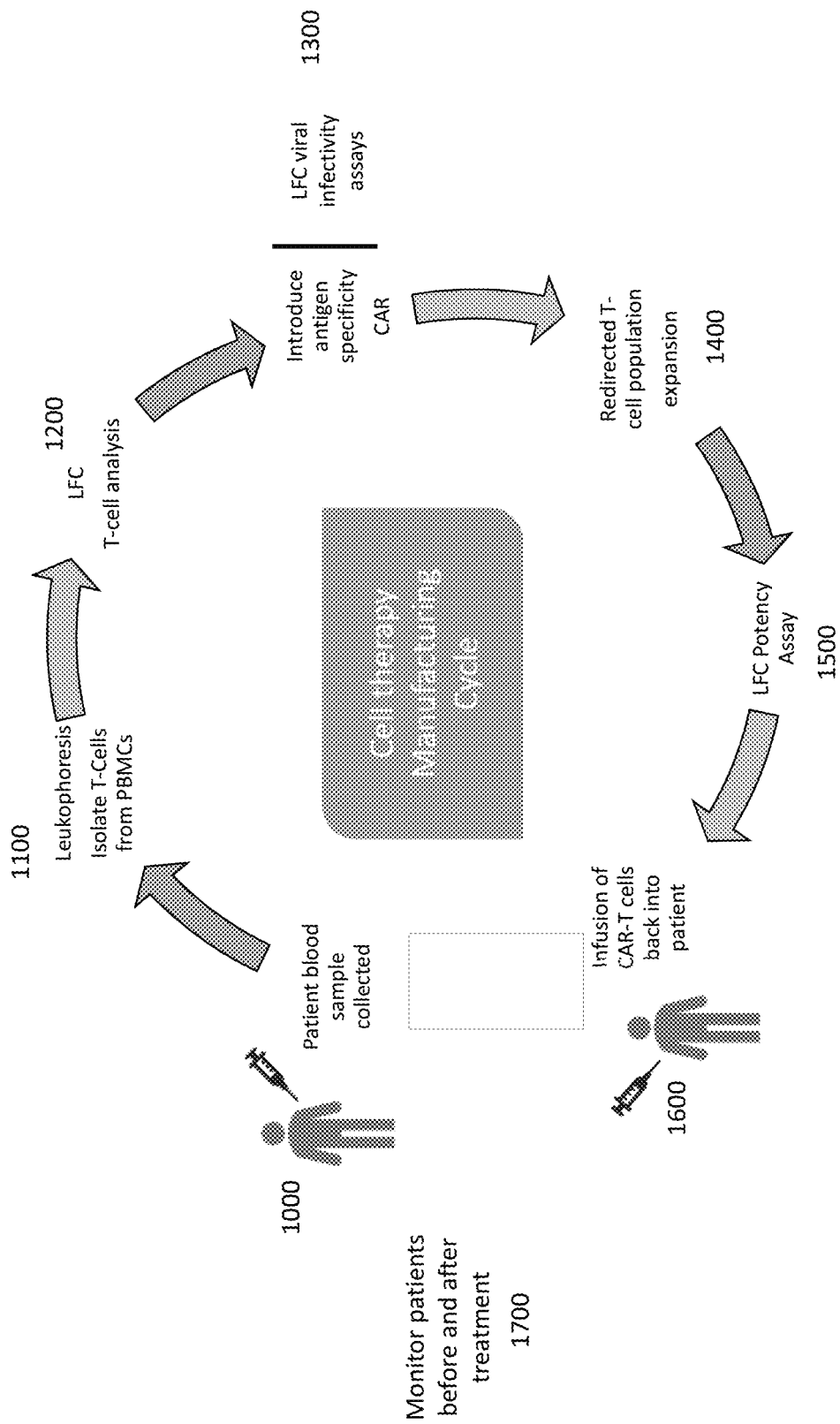
FIG. 10 is a schematic depicting the cell therapy biomanufacturing cycle and specific areas of application for laser force technology.

In an embodiment, the use of LFC for characterization of cell therapy biomanufacturing and use is accomplished using a series of novel methods. The range of applications, as shown in FIG. 10, begins with analysis of the input cells as starting materials. The range of genetic diversity, cell condition and environmental variability is a major source of difficulty in the efficient and efficacious processing of cells for cell therapy applications. Understanding and accounting for the variability as taught herein improves the manufacturing process and ultimately, patient outcomes. In an embodiment, blood cells are removed from the patient (1000) and undergo apheresis for collection of the T-cells (1100). LFC can be applied (1200) to characterize the whole blood sample or any cell fraction thereof for phenotypic markers that may prove diagnostic for biomanufacturing. RADIANCE™ (LumaCyte, Charlottesville, Va. USA) (or other optical force based instruments) may be used to identify phenotypes in either PBMC or T-cell samples that may predict of manufacturing success or failure and may indicate remedies. This quantitative measurement of variation in patient PBMC and T-cells may provide predictive (if the biomanufacturing will be successful) or prescriptive (what to do to make the biomanfacturing effort successful) analytics for assessing the value of therapy for a given patient or making changes to the cell processing to achieve success. The RADIANCE™ device is a preferred instrument for use as it enables the characterization and sorting of individual cells by measuring their optical force; differences in cell biochemistry, morphology, and deformability (cytoskeletal changes), which are often associated with cancer, and other diseases, give rise to detectable differences in optical force and deformability, which are quantitated by RADIANCE™.

Figure 11:
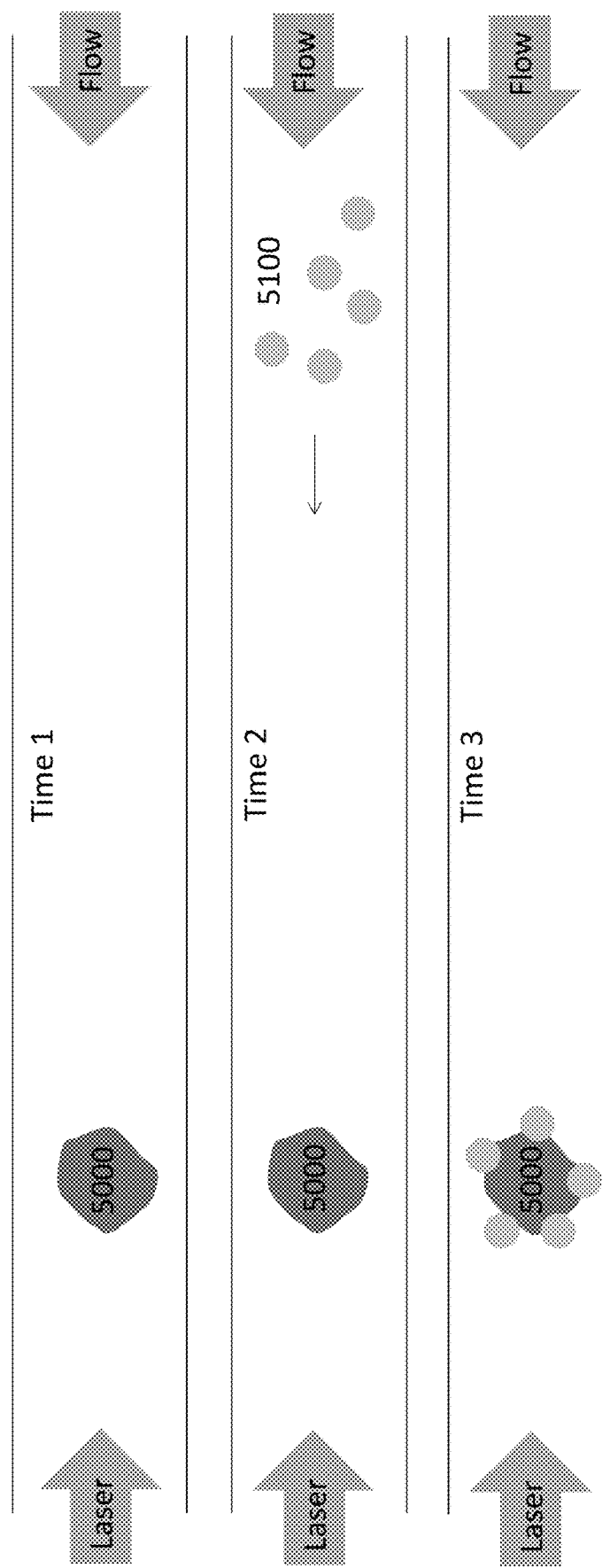
FIG. 11 is a schematic depicting introduction of cell therapy products to target cells or particles. The schematic shows a single target cell, however, it would be possible to introduce multiple target cells simultaneously in a multibeam array or simply in a line, in order to determine for example, how many target cells (such as cancer cells) are bound or captured by a known quantity of introduced cell therapy products.

The T-cell, or other sub-population of cells, may be measured as part of an infectivity assay for lentivirus, retrovirus, adeno associated virus or any other virus used to modify the cells during production (1300). Production process monitoring is an important part of the biomanufacturing process where LFC instrumentation can be used for on-line monitoring of cellular parameters during cell expansion to count cells and identify phenotypic markers that indicate production performance (1400), including non-viral based cellular modification as well as changes in environmental or other process conditions that may affect the cells or process performance. RADIANCE™ or other optical force based instruments can identify and quantitate the potency of engineered T-cells (1500) and also perform a co-culture assay with relevant target cell line to measure the killing power of the engineered cells prior to infusion in the patient (1600). LFC can also be used to measure the patients' response to the cell therapy treatment by collecting blood or biopsy samples and analyzing the cells for phenotypic changes due to the cell therapy (1700). FIG. 11 shows the introduction of cell therapy products to a trapped target cell for the purpose of measuring binding and killing efficiency. The target cell could be a cancer cell, either primary or a cell line, or any type of cell engineered to express target molecule. Initially, a target cell (5000) or group of cells is introduced into the system and trapped using optical forces (Time 1). Subsequently, a population of product cells (5100) are introduced while the target cell is still trapped (Time 2). If the product cells have an affinity for the target cell, they will bind to it as shown (Time 3). This represents an automated binding and potentially killing co-culture experiment using LFC. Once bound, additional parameters can be measured in a static and dynamic fashion as described in subsequent figures. As an alternative to a target cell, another substance such as a bead, particle, or vesicle with the appropriate target molecule attached could be used.

Figure 12:
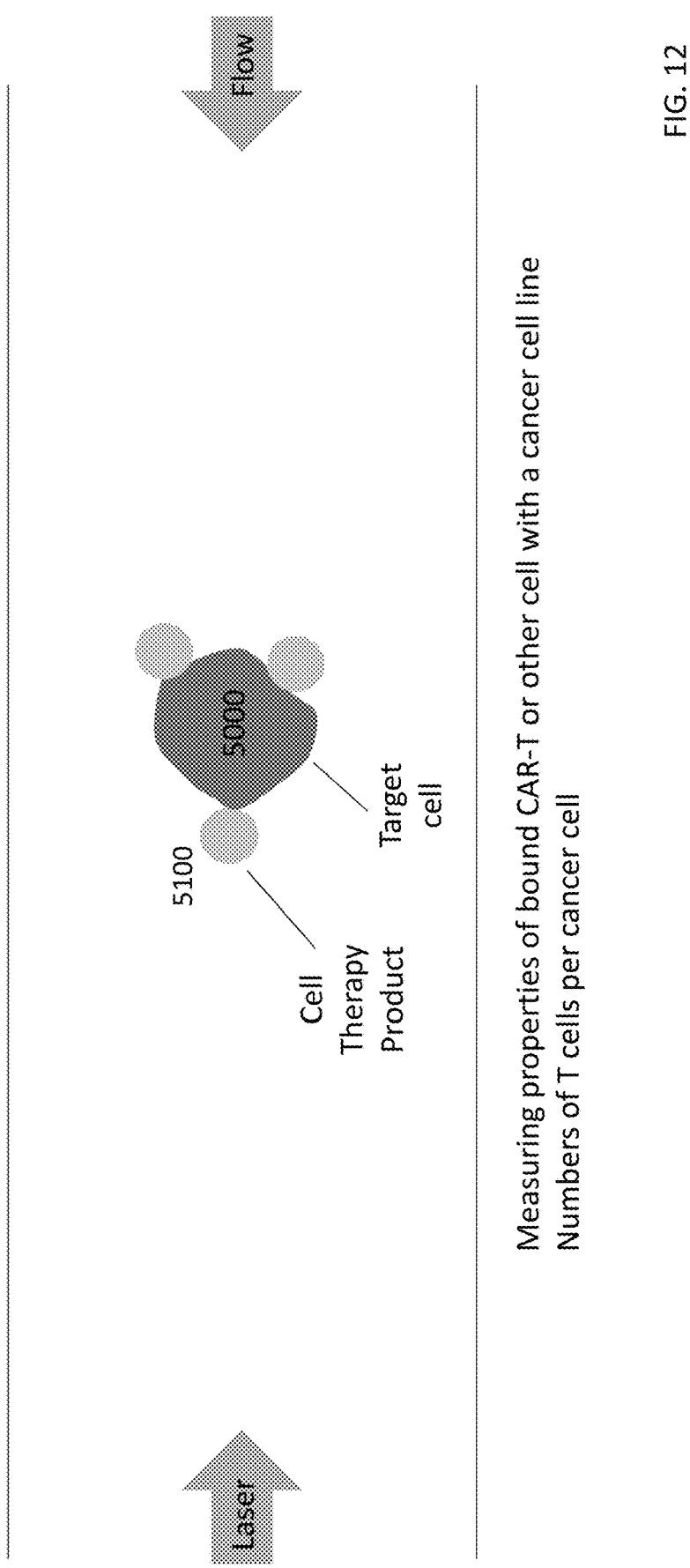
FIG. 12 is a schematic depicting the measuring of a complex of one or more cell therapy product cells interacting with one or more target cells or particles. The parameters measured include properties of the bound CAR-T or other product cells with the target cells, including for example the number of T cells bound per target cell.
Figure 13:
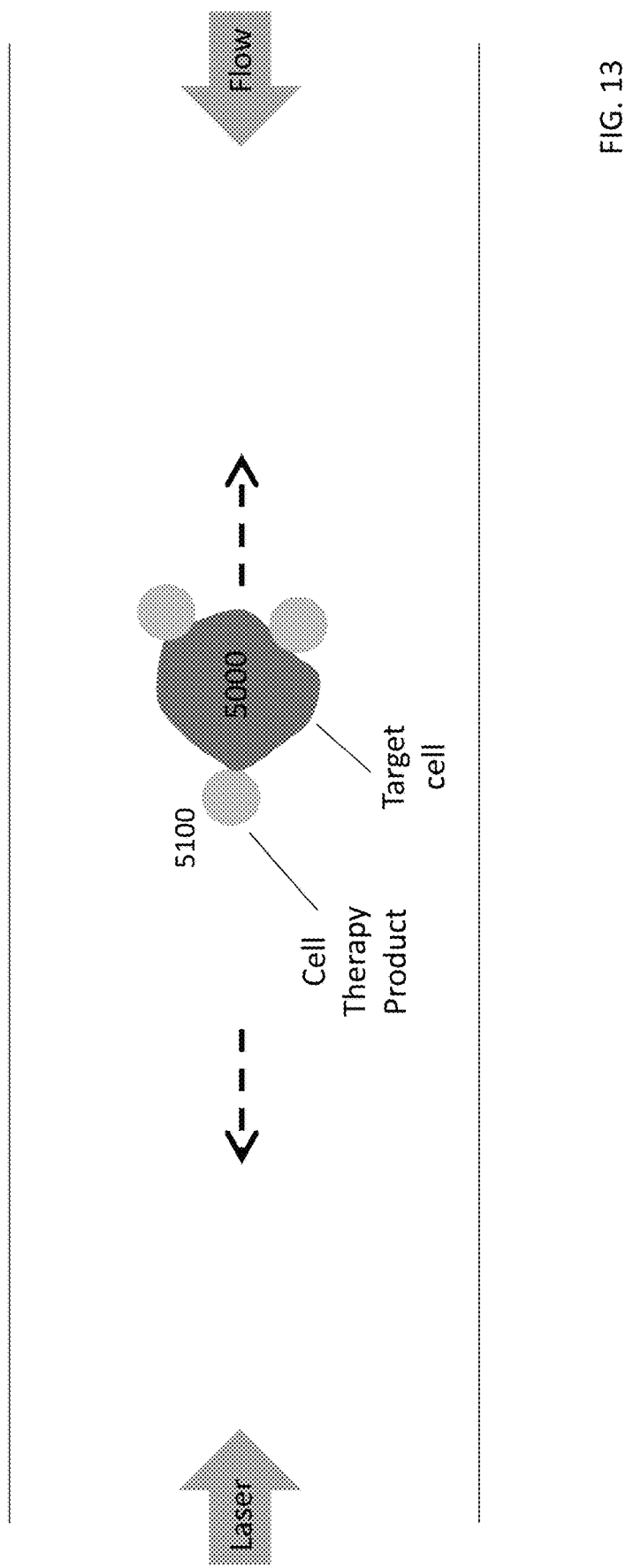
FIG. 13 is a schematic demonstrating the use of flow and laser forces to assess cell therapy product and target cell binding strength and properties. In certain embodiments, the cells or cell complexes may be moved back and forth by changing conditions (laser, flow, etc.) to disrupt bonds and break apart the cell complexes. The information gathered by such analysis enables the understanding of binding dynamics and bond strength for cell binding strengths; such methods are useful and applicable for the selection, characterization, and production of CAR-T candidates against cancer cells.
Figure 14:
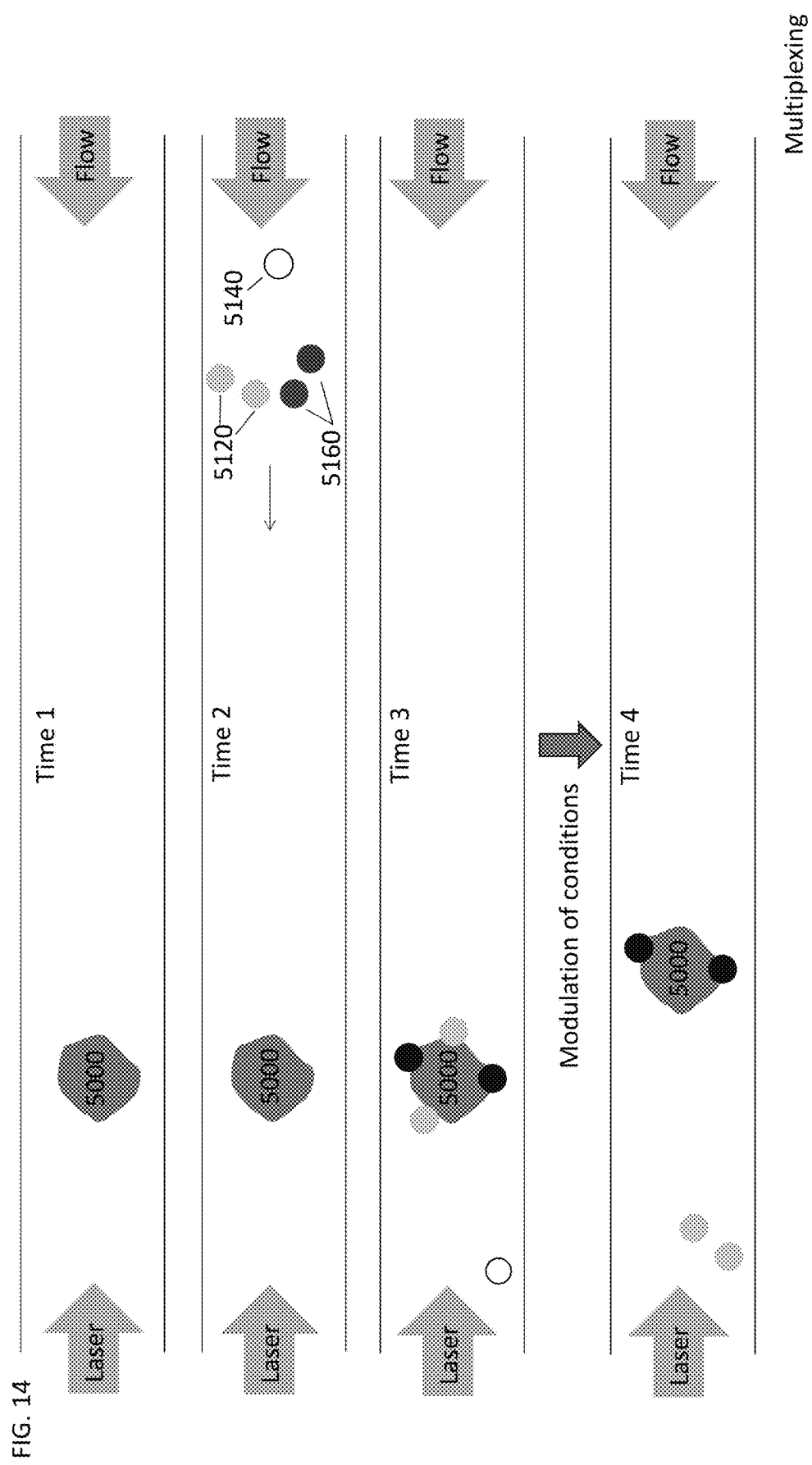
FIG. 14 is a schematic showing the introduction and measurement of an assortment of cell therapy products interacting with target cells, including a change in interaction of such products following modulation of conditions.

FIG. 12. shows a target cell and a cell therapy product (CAR-T cell for example) bound together as part of the co-culture experiment wherein a T-cell sample is incubated with a target cell (either a primary patients' cell or a relevant cell line) prior to introduction to the system or analysis channel for a pre-determined amount of time. By measuring LFC parameters under varying levels of flow and laser power, a profile can be established for each patients' engineered cells and their affinity for cancer cells and ability to destroy them. The process can be monitored post culture or conducted in real-time to observe the effects of the cancer cell killing. The diagnostic value of measuring the LFC time kinetics of the killing assay is significant and represents a valuable quality indicator or critical quality attribute (CQA) for understanding the success of the biomanufacturing and the resulting efficacy in patient. In some cases, there may also be free (unbound) target cells as well as free product cells that can be analyzed as part of the overall population. In this mode of operation, the cells or complexes can be analyzed by trapping individual cells and measuring their properties, or by continuously flowing cells or complexes through the system. For either trapped or continuously flowing cells or complexes, numerous parameters can be measured related to the optical forces of the cells, the number of product cells bound per target cell or particle, the size and shape of the cells or complexes, or other intrinsic parameters. In addition, other detection methods may be used to interrogate the cells or complexes, including but not limited to a standard light scatter detector, a standard single wavelength fluorescent detector, a standard spectroscopic fluorescent detector, a standard CCD camera, a standard CMOS camera, a standard photodiode, a standard photomultiplier tube, a standard photodiode array, a standard chemiluminescent detector, a standard bioluminescent detector, and/or a standard Raman spectroscopy detector. FIG. 13. Shows a variation on the method to analyze the cell therapy product and cancer cell bound complex wherein the laser force, fluid flow, or a combination thereof can be modulated in order to shuttle the complex back and forth aggressively to disrupt cellular bond(s) and release cells or activate the cells to generate additional metrics for analyzing cellular parameters to characterize product quality. Understanding the binding dynamics and bond strength for cell binding is applicable for the assessment of engineered cell therapy cells against cancer cell lines. All of these methods can be multiplexed to accommodate parallel analysis using multiple channels and/or lasers for rapid analysis. FIG. 14. shows the introduction of an assortment of different product cell types or batches to a trapped target cell (5000). In this case, only certain types may bind to the target cells initially. In FIG. 14, 3 different product cells (5120, 5140, and 5160) are introduced, with only two of the three (5120 and 5160) binding to the target cell while the other type (5140) does not bind and flow through the channel. This technique may be used to further screen different types of product cells, that may be differentiated based on a number of factors, including but not limited to genetic differences in the non-modified product cell, differences between the genetic modifications made to the cell, differences in cell processing, growth, or activation, or other conditions or changes that may affect product cell quality or performance. Once an initial cohort of cells have been bound to the target cell, flow or laser conditions may be altered to affect the binding dynamics of the target cells such that a smaller subset is bound (shown in Time 4). This may be used as another way to screen product cells for binding affinity and strength. Several methods are contemplated to determine which product cells are bound, including fluorescence, bar coding, or other genetic or phenotypic analysis. This analysis may be conducted at any time, for example while the cells are trapped in the system or subsequently by collecting the complexes after processing.

Figure 15:
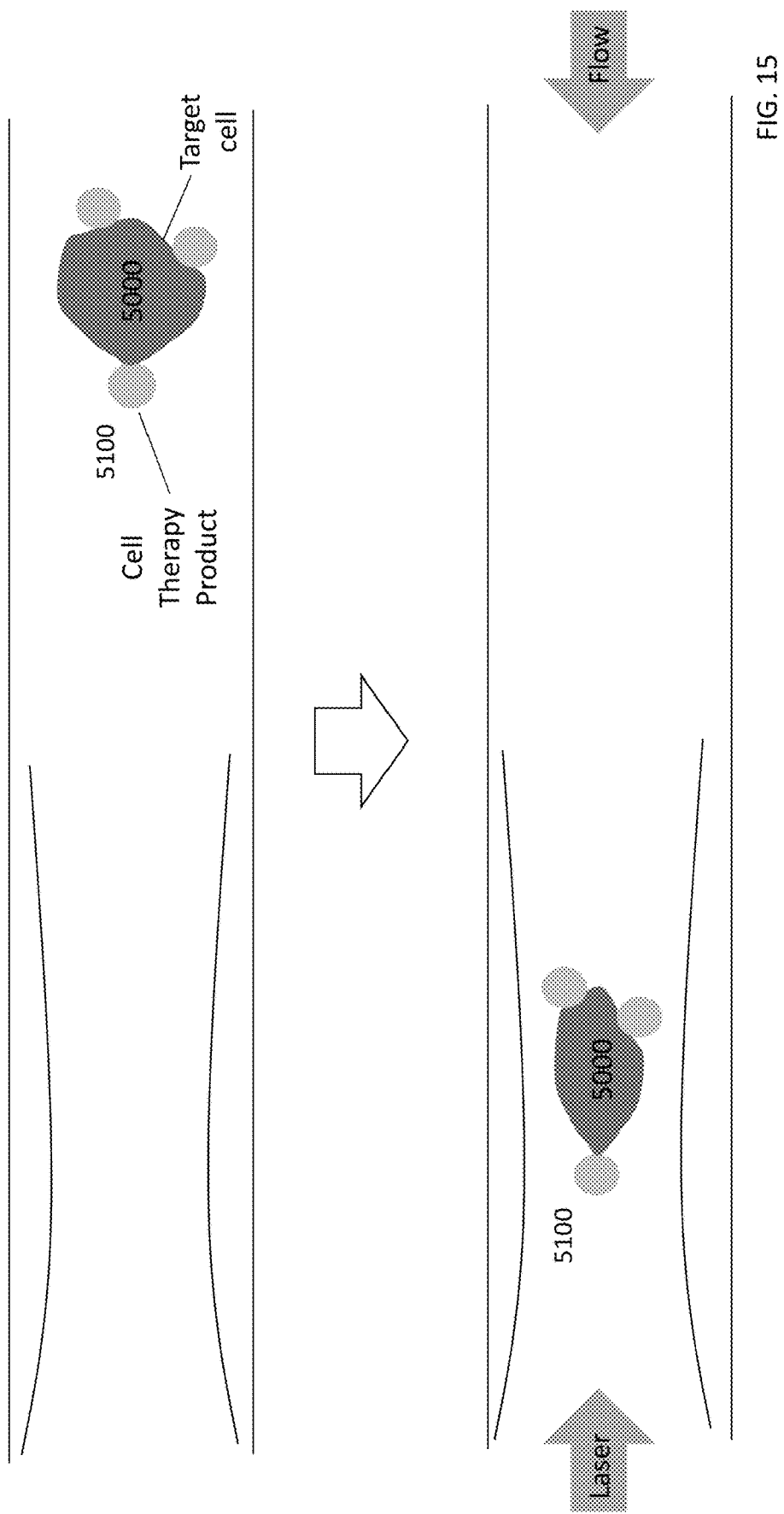
FIG. 15 is a schematic showing measuring target cell dynamics in response to cell therapy treatment. In certain embodiments, target cells including tumor cells may be treated with CAR-T cells and then deformability and other properties may be measured as a metric for tumor cell killing efficacy or other properties of interest. The target cell may be measured bound to the CAR-T cells or detached.

FIG. 15 shows the measurement of changes in target cell dynamics as a result of cell therapy product binding. The assay can be run in the presence or absence of laser forces and with varying degrees of fluidic flow (drag force) and laser power (optical force) to induce varying levels of opposing forces on the target cells. One embodiment is shown in FIG. 15 in which a complex consisting of a Target Cell (5000) and one or more Cell Therapy Products (5010) enters the channel (top portion of the image). As the complex moves into the area of laser interaction, the Target Cell deforms as a result of the combined optical and fluidic force (bottom portion of the image). Measurements can be made initially or over a period of time in order to monitor the dynamic effects of the bound product cells, in order to quantify cell therapy product potency or cell therapy product killing efficiency or capacity. These measurements include but are not limited to cell deformability, optical force and other optical force or shape-based measurements.

The invention will be further described with reference to the following example; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

Example 1

Assessment of T-Cell Activation

Figure 16:
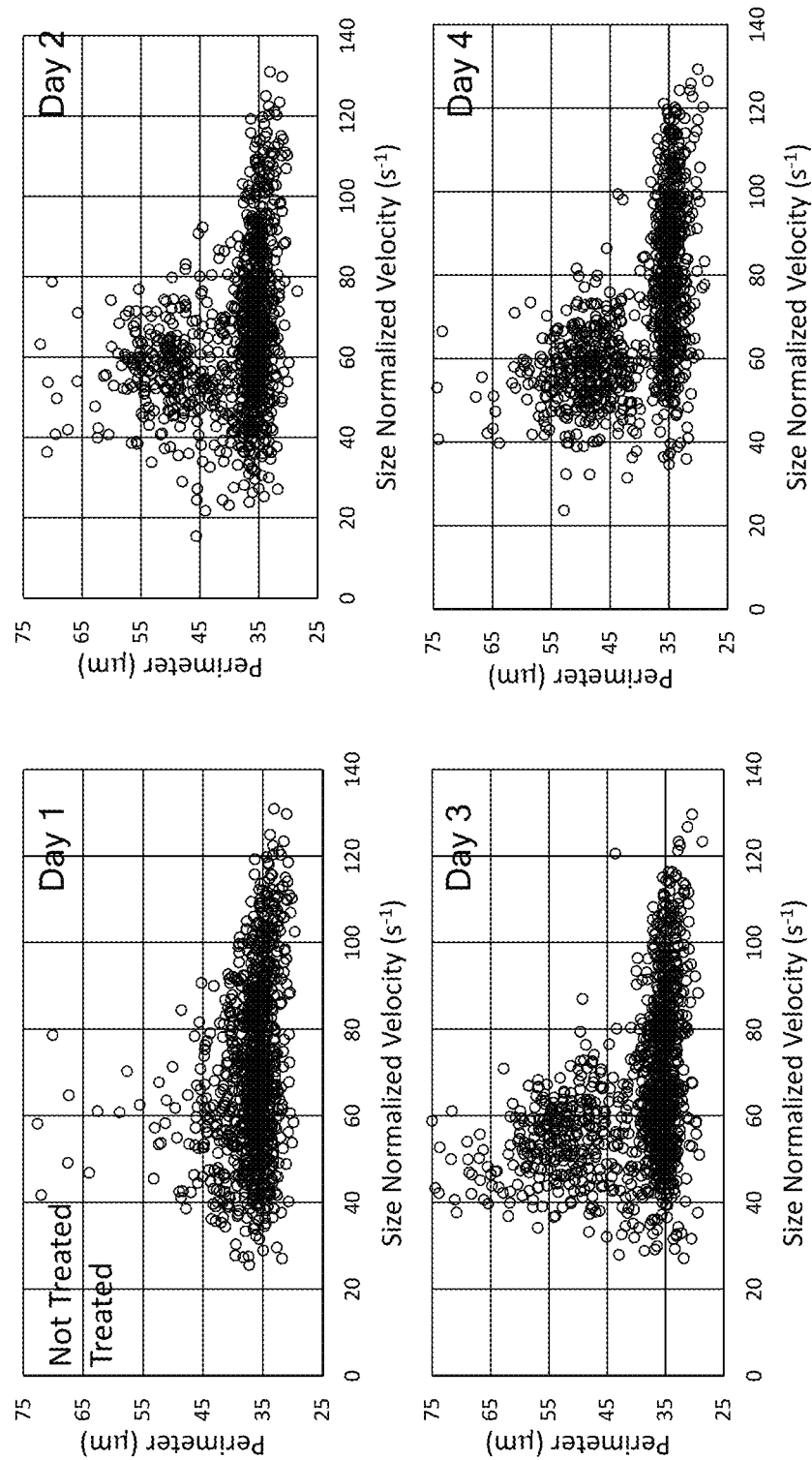
FIG. 16 is a series of scatter plots demonstrating the progression of T-cell activation over a 4 days period as measured in a label-free manner using Laser Force Cytology. Human T-cells were treated on Day 0 with StemCell Technologies ImmunoCult Human CD3/CD28 activator and sampled each day using a RADIANCE™ instrument. Changes in both the Size Normalized Velocity and Perimeter are shown as a result of treatment and can be used to monitoring T-cell activation, an important step in the biomanufacturing process for CAR-T and TCR therapies. Since the technology is label-free, variation in patient cells cannot affect the activation measurement, nor is the time delay, labor, and expense of antibody labelling required for monitoring.

Frozen Human Peripheral Blood Pan-T cells were obtained from a commercial source. The cells were thawed into medium and seeded into 96 well plates at a concentration of 1e6 cells/mL. Treated cells received 5 µL of IMMUNOCULT™ (STEMCELL™ Technologies, Vancouver Canada) activator per well (200 µL), while untreated cells received only medium (mock). Cells were treated on Day 0 and both treated and untreated cells were harvested every 24 hours for 4 days starting on Day 1. Harvested cell samples were centrifuged and the pellet was resuspended in LUMACYTE™ (Charlottesville, Va.) stabilization fluid at a concentration of approximately 5e5 cells/mL prior to analysis with a RADIANCE™ instrument. A portion of each cell sample was also fixed and labeled with a CD25 antibody and measured using a flow cytometer in order to confirm activation. Changes were seen in multiple parameters as a result of treatment demonstrating the potential to monitor T cell activation in a rapid label-free manner. Shown in FIG. 16 are the changes in Size Normalized Velocity and Perimeter. Additionally, differing activators cause varying response in T-cells indicating the ability to assess the nature of the activation for analytical purposes in both biomanufacturing and patient diagnostics. Since the present technology is label-free, variation in patient cells cannot affect the activation measurement, nor is the time delay, labor, and expense of antibody labelling required for monitoring. Accordingly, this Example highlights the utility of the methods described herein.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary or explanatory in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method for assessing biological particles for use in cell immunotherapy, comprising the use of a device wherein the device comprises:
   the use of a substrate comprising a plurality of channels configured to transport one or more biological particles, wherein the plurality of channels comprises:
   a first channel disposed vertically within the substrate,
   a second channel in operable communication with the first channel and disposed horizontally within the substrate,
   a third channel in operable communication with the second channel and disposed vertically within the substrate, and
   a fourth channel in operable communication with the third channel and disposed horizontally within the substrate;
   wherein the first, second, third and fourth channels are disposed in such a manner as to provide a path for movement of the one or more biological particles through the substrate from the first channel to the second channel to the third channel to the fourth channel,
   injecting one or more biological particles into the first channel disposed vertically within the substrate through a bottom horizontal planar surface having an opening to the first channel, to maintain directional and volumetric continuity with the first channel,
   wherein the biological particles comprise T-cells, engineered T-cells, including CAR T cells,
   assessing the biological particles via optical force-based measurements,
   wherein the optical force-based measurements are used to yield information pertaining to morphology, motility, binding affinities, binding profiles, effect on other biological particles, effect on target cells, susceptibility to external forces such as biological, biochemical, chemical, physical, and temperature influences.

2. The method of claim 1, wherein the assessment comprises a quantitative measurement of variation in the T-cells and provides predictive or prescriptive analytics.

3. The method of claim 1, wherein the bottom horizontal planar surface has at least one shorter length from one edge to another edge compared to at least one length from one edge to another edge on a vertical planar surface of the substrate to maintain directional and volumetric continuity with the first channel.

4. The method of claim 1, wherein the one or more biological particles is injected into the first channel disposed vertically within the substrate through a bottom horizontal planar surface having an opening to the first channel, wherein the bottom horizontal planar surface has a smaller or equal surface area compared to a surface area on a vertical planar surface of the chip, in a vertical direction to maintain directional and volumetric continuity with the first channel.

5. The method of claim 1, wherein the first channel comprises an opening disposed at an exterior surface of the substrate and in such a manner as to provide a path for the one or more biological particles to enter vertically into the substrate and to move vertically within the first channel.

6. The method of claim 1, further comprising a collimated or focused light source oriented to interact with biological particles or cells in the fourth channel.

7. The method of claim 1, wherein a collimated or focused light source is oriented to propagate in the direction of, opposite the direction of, orthogonal to the direction of, or diagonal to the movement of the one or more biological particles in the fourth channel.

8. The method of claim 1, wherein the fourth channel allows for imaging and analysis of biological particles or cells during movement of the one or more biological particles or cells, and from multiple focal planes, angles, and/or orientations by one or more imaging devices.

9. The method of claim 1, further comprising one or more electrical force, optical force, and/or fluidic force to move biological particles or cells in one or more channels.

10. The method of claim 1, wherein the plurality of channels comprises a fifth channel, which splits into two or more channels or wells to sort cells or particles.

11. The method of claim 1, further comprising an imaging device selected from at least one of a bright field imager, a light scatter detector, a single wavelength fluorescent detector, a spectroscopic fluorescent detector, a CCD camera, a CMOS camera, a photodiode, a photodiode array (PDA), a spectrometer, a photomultiplier tube or tube array, a photodiode array, a chemiluminescent detector, a bioluminescent detector, a standard Raman spectroscopy detection system, surface enhanced Raman spectroscopy (SERS), coherent antistokes Raman spectroscopy (CARS), and/or coherent stokes Raman spectroscopy (CSRS).

12. The method of claim 1, wherein laser force cytology (LFC) is used to assess the biological particles or cells.

13. The method of claim 12, wherein the use of LFC comprises the combination of microfluidics and light-induced pressure to take measurements comprising optical force, pressure, size, and velocity on a per cell basis.

14. The method of claim 12, wherein the use of LFC is used to assess characteristics of biological particles, wherein the characteristics comprise morphology, motility, interaction of the biological particles with other physiological components, deformability (cytoskeletal changes), or reaction of the biological particles to environmental changes.

15. The method of claim 1, wherein the assessment of biological particles comprises the measuring of a complex of one or more cell therapy product cells interacting with one or more target cells or particles.

16. A method for assessing biological particles for use in cell immunotherapy, comprising the use of a device wherein the device comprises:
   the use of a substrate comprising a plurality of channels configured to transport one or more biological particles, wherein the plurality of channels comprises:
      a first channel disposed vertically within the substrate,
      a second channel in operable communication with the first channel and disposed horizontally within the substrate,
      a third channel in operable communication with the second channel and disposed vertically within the substrate, and
      a fourth channel in operable communication with the third channel and disposed horizontally within the substrate;
   wherein the first, second, third and fourth channels are disposed in such a manner as to provide a path for movement of the one or more biological particles through the substrate from the first channel to the second channel to the third channel to the fourth channel,
   injecting one or more biological particles into the first channel disposed vertically within the substrate through a bottom horizontal planar surface having an opening to the first channel, to maintain directional and volumetric continuity with the first channel,
   wherein the biological particles comprise T-cells, engineered T-cells, including CAR T cells,
   assessing the biological particles via laser force cytology (LFC) measurements
   wherein the LFC measurements are used to yield information pertaining to morphology, motility, binding affinities, binding profiles, effect on other biological particles, effect on target cells, susceptibility to external forces such as biological, biochemical, chemical, physical, and temperature influences.

17. The method of claim 16, wherein the use of LFC comprises the combination of microfluidics and light-induced pressure to take measurements comprising optical force, pressure, size, and velocity on a per cell basis.

18. The method of claim 16, wherein the use of LFC is used to assess characteristics of biological particles, wherein the characteristics comprise morphology, motility, interaction of the biological particles with other physiological components, deformability (cytoskeletal changes), or reaction of the biological particles to environmental changes.

19. The method of claim 16, wherein the assessment of biological particles comprises the measuring of a complex of one or more cell therapy product cells interacting with one or more target cells or particles.

20. The method of claim 16, wherein the assessment of biological particles comprises characterization of cells for efficacy assays, characterization of cells for potency assays, CAR-T cell affinity studies, CAR-T cell binding studies, detection of T-cell biomarkers, or label-free detection of T-cell activation.

* * * * *